(12) United States Patent
Noishiki

(10) Patent No.: US 7,833,148 B2
(45) Date of Patent: Nov. 16, 2010

(54) LUMEN FORMATION-INDUCIBLE MATERIAL AND INSTRUMENT TO BE INSERTED INTO THE BODY

(75) Inventor: Yasuharu Noishiki, 6-11-301, Namiki 2-chome, Kanazawa-ku, Yokohama-shi, Kanagawa 236-0005 (JP)

(73) Assignee: Yasuharu Noishiki, Kanagawa (JP)

( * ) Notice: Subject to any disclaimer, the term of this patent is extended or adjusted under 35 U.S.C. 154(b) by 1152 days.

(21) Appl. No.: 10/498,522

(22) PCT Filed: Dec. 13, 2002

(86) PCT No.: PCT/JP02/13084

§ 371 (c)(1),
(2), (4) Date: Jun. 14, 2004

(87) PCT Pub. No.: WO03/051420

PCT Pub. Date: Jun. 26, 2003

(65) Prior Publication Data

US 2005/0084511 A1    Apr. 21, 2005

(30) Foreign Application Priority Data

Dec. 14, 2001    (JP) .............................. 2001-381833

(51) Int. Cl.
A61F 2/00    (2006.01)
(52) U.S. Cl. ...................................... 600/36
(58) Field of Classification Search .................. 600/36; 128/897–899; 623/1.1–1.54
See application file for complete search history.

(56) References Cited

U.S. PATENT DOCUMENTS

| | | | |
|---|---|---|---|
| 3,710,777 A | 1/1973 | Sparks | |
| 4,820,626 A | 4/1989 | Williams et al. | |
| 5,415,619 A | 5/1995 | Lee et al. | |
| 5,766,584 A | 6/1998 | Edelman et al. | |

FOREIGN PATENT DOCUMENTS

| EP | 382158 | 8/1990 |
|---|---|---|
| JP | 576588 | 3/1993 |
| JP | 6125980 | 5/1994 |
| JP | 9308693 | 12/1997 |
| WO | WO 8002641 | 12/1980 |
| WO | WO 9608222 | 3/1996 |
| WO | WO 9638188 A1 | 12/1996 |
| WO | WO 01/97874 A1 | 12/2001 |
| WO | WO 02/10221 A1 | 2/2002 |

OTHER PUBLICATIONS

Noishiki, Y. "Method for inducing the growth of new arteries in the myocardium" Jpn J. Thorac Cardiovasc Surg, 54:319-327 (2006).

*Primary Examiner*—John P Lacyk
(74) *Attorney, Agent, or Firm*—Millen, White, Zelano & Branigan, P.C.

(57) ABSTRACT

The present invention discloses a fistula formation-inducing material having a property of forming a fistula wherein cells are exposed on at least a portion of the fistula luminal surface. This material can be inserted into a living body, using a hollow tubular member, as desired. As a result, there is provided a fistula formation-inducing material which allows the formation of a fistula, reliably lined by host cells, in a living body.

18 Claims, 27 Drawing Sheets

LUMEN FORMATION-INDUCIBLE MATERIAL AND INSTRUMENT TO BE INSERTED INTO THE BODY

TECHNICAL FIELD

The present invention relates to a fistula formation-inducing material having a surface capable of inducing fistula formation. More particularly, the present invention relates to a fistula formation-inducing material capable of being preferably used for an artificial fistula formation in vivo.

In a case where the fistula formation-inducing material according to the present invention is used, e.g., when tissues or organs of a living body (or living organism) are pierced with a fiber of the material, i.e., a mandrel, a tissue fistula (or cavity) can be inductively formed, wherein cells are exposed on the fistula luminal surface around the mandrel. After the fistula formation with host cell lining, the mandril is removed and/or caused to disappear by a certain means so as to substantially leave only the fistula covered with host cells. A fistula can be artificially formed in the living body wherein the luminal surface of the fistula is covered by the cells.

Although the size of the tissue fistula of the fistula formation-inducing material according to the present invention can be determined according to the thickness or diameter of the mandrel to be used, the tissue fistula can have an internal diameter of, e.g., from about 0.1 mm to about 8 mm. In a specific example, when a mandril having an external diameter of about 2 mm is inserted into the cardiac wall, it is possible to create a fistula having a thickness corresponding to the mandril thickness in the site wherein the mandril is present (namely, a long, narrow fistula having an internal diameter of 2 mm can be formed within the muscle layer of the cardiac wall). When such a long, narrow fistula is formed in this manner, blood begins to flow through the fistula so that the fistula can be caused to function as a blood vessel.

Other specific examples may include the formation of a fistula having an inner diameter of about 0.5 mm for draining aqueous humor from the ophthalmus to reduce intraocular pressure associated with glaucoma, as well as fistula preservation during various surgical procedures such as fistuloplasty, tracheoplasty, cholangioplasty, enteroplasty, urethroplasty, salpingoplasty and funiculoplasty. The present invention relates to the artificial formation of such fistulae in a living body, and so forth.

BACKGROUND ART

Heretofore, it has been considered to be very difficult to form a narrow tissue fistula having an internal diameter of, for example, 6 mm or less in a living body, etc. In particular, there has been no technique for forming a tissue fistula having an internal diameter of 3 mm or less. However, there are several known methods for forming a comparatively wider tissue fistula, and methods using a mandrel are also known. Specific examples of known methods of forming a fistula by inserting a (comparatively thick) mandril, may include a method wherein cells are attached outside a living body, and a technique for attaching cells in a living body.

A typical example of the technique for the method of forming a tissue in a living body is U.S. Pat. No. 3,710,777 filed by Sparkes. In this technique, a metal pipe is inserted in coincidence with the location where a blood vessel implantation is to be performed in advance within the subcutaneous tissue of the thigh in a patient with an occluded femoral artery, and a combination wherein an artificial blood vessel made of Dacron fabric (trade name, polyester fiber, Dupont) is covered around the outside of a silicone rod having an outer diameter of 6-8 mm, is inserted within the pipe, and then only the metal pipe is extracted therefrom. As a result, the combination of a silicone rod and fabric artificial blood vessel is allowed to remain in the subcutaneous tissue in the site where the blood vessel implantation is to be performed.

In this manner, when the silicone rod is removed after a predetermined time period (e.g., 3 months) has elapsed, since cells are entangled with the fabric artificial blood vessel, a tissue fistula is formed wherein the fibers of the fabric artificial blood vessel serve as a framework at the location where the blood vessel implantation is to be performed on the patient. U.S. Pat. No. 3,710,777 discloses such a technique wherein an artificially formed tube is used as an artificial blood vessel in the site of the patient's own occluded femoral artery.

The above-mentioned Sparkes technique is commercially available under the name of the Sparkes mandril graft, and is widely used clinically. However, when this type of mandril graft is actually used, tissue formation in a living body does not proceed as would be expected, and the mandril must be inserted in a living body for a period of at least three months in order to obtain reliable tissue formation. In addition, the adherence of cells to the fibers of the fabric is poor, even in the case of the insertion into a living body for such a long period of time. Further, since the tissue formation tends to be incomplete at the portion which contacts with the silicon rod on the inside of the Dacron fabric in particular, the above product has been reported to be unable to fulfill the function of an artificial blood vessel (see Hallin R W, Sweetman W R: The Sparkes' Mandril Graft—A seven year follow-up of mandril grafts placed by Charles H. Sparkes and his associates, American Journal of Surgery, 132; 221-223, 1976). In consideration of these circumstances, the Sparkes mandril graft was gradually used less and is currently not used at all.

In the above-mentioned Sparkes technique, a silicone rod is placed in contact with the luminal surface of the above-mentioned Dacron (polyester fiber) fabric, and is inserted into a living body. According to the approach adopted by Sparkes, cells are expected to infiltrate into the interstices between the fibers of the Dacron fabric. However, as the Dacron fibers are coated with silicone and the coated silicone is present in contact with the Dacron fibers, the infiltration and migration into the interstices of the physiologically inactive silicone as well as mitosis and other cell activities are inhibited, and the circulation of body fluid, for supply of nutrition to the cells, is also impaired. That is, the prolonged presence of the silicone in a living body impaired the tissue formation at the portion in contact with the silicone because it is a non-physiological substance.

Such non-physiological substances are typically surrounded by a tissue containing large amount of collagen fibers generally referred to as scar tissue. In pathological terms, this is referred to as "encapsulation". Accordingly, in the case of the Sparkes technique, the rich collagen tissue is formed due to this encapsulation phenomenon, and it is extremely rare for cells to be exposed on the surface thereof.

Moreover, in the Sparkes technique, the above-mentioned Dacron (polyester fiber) artificial blood vessel is essential. A tissue fistula is formed as a result of cells adhering to these Dacron fibers. Accordingly, the presence of these Dacron fibers is essential.

As a technique for forming tissue in a living body is considered to be theoretically superior for the growth and migration of cells in a living body, attempts have been repeated by using new techniques. A typical example of such an attempt is disclosed in U.S. Pat. No. 5,171,261, which describes an effective technique for slicing tissue into thin sections, and disseminating the resultant tissue sections so as to implant them in the form of an artificial blood vessel. In addition, other techniques have also been developed for forming vascular-like tissue in a living body as disclosed in U.S. Pat. Nos. 5,849,036 and 5,399,352.

Auxiliary techniques for forming a fistula in a living body in regions other than blood vessels may be used for preserving the form of a fistula for treatment of constriction of the nasolacrimal duct. Examples of the prior art relating to these techniques include U.S. Pat. Nos. 6,238,370, 6,082,362, 5,423,777, 4,959,048 and 4,380,239.

Other examples include techniques used for the bile duct and during constriction of the esophagus, and such techniques are described in U.S. Pat. Nos. 5,716,981 and 5,120,322. However, these techniques do not intentionally form a narrow fistula by using surrounding cells.

An extremely large number of examples of the prior art have been reported and relate to filamentous substances which are degraded and absorbed in a living body. These techniques were reported a long time ago as is evidenced by, for example, U.S. Pat. No. 3,976,071. Moreover, there are numerous other examples of this technique, including U.S. Pat. Nos. 5,010,145, 6,063,117 and 5,584,836. Moreover, examples of prior art simultaneously using a cell growth factor and cells, etc., include U.S. Pat. Nos. 5,386,012 and 5,885,829, while U.S. Pat. No. 5,614,515 reports a technique used for the purpose of preventing adherence.

Although there are several other techniques which are used in the form of fibers or filaments using substances which are degraded and absorbed in a living body, there has been no technique for forming a fistula within various organs and tissues, nor a technique which uses such a technique to form various types of tissue fistula (namely, technique for forming and inducing artificial tissue fistula).

DISCLOSURE OF THE INVENTION

An object of the present invention is to provide a fistula formation-inducing material which can overcome the above-mentioned disadvantages encountered in the prior art.

Another object of the present invention is to provide a fistula formation-inducing material which can induce reliable fistula formation with a host-cell lining, on its luminal surface, in a living body.

As a result of earnest study, the present inventor has found that the use of a fistula formation-inducing material having a property of forming "a fistula luminal surface on which cells are exposed on at least a portion thereof" is extremely effective for achieving the above-mentioned object.

The fistula formation-inducing material according to the present invention is based on the above-mentioned finding, and more specifically, it is a fistula formation-inducing material having a property of forming a fistula wherein cells are exposed in at least a portion of the fistula luminal surface.

The present invention also provides a device for body insertion, comprising: a hollow tubular member and a fistula formation-inducing material, at least a portion of which is inserted into the hollow tubular member; wherein the fistula formation-inducing material has a property of forming a fistula wherein cells are exposed on at least a portion of the fistula luminal surface.

The present invention further provides a fistula-forming method, comprising: disposing a fistula formation-inducing material in a tissue, retaining the fistula formation-inducing material in the tissue for a predetermined time period, and removing, and/or causing to disappear, at least a portion of the fistula formation-inducing material to thereby form a fistula in the tissue;

wherein the fistula formation-inducing material has a property of forming a fistula wherein cells are exposed in at least a portion of the fistula luminal surface.

In the present invention, by using a fistula formation-inducing material, which comprises a solid material (e.g., material having biodegradable polymer as a constituent component) to which fibrin and/or platelets do not adhere (e.g., having cellular non-adherence and/or antithrombogenicity), cells are made to carry out tissue remodeling in tissue and organs of a living body and, as a result, the formation of a tissue fistula (namely, fistula wherein the luminal surface is covered by cells) can be induced by peripheral cells centered about a mandril.

In a case where, having arranged the fistula formation-inducing material according to the present invention in a living body, adherence and/or infiltration of fibroblasts to the surface of the fistula formation-inducing material is prevented based on its fibrin and/or platelet non-adherence, and as a result of capillaries extending towards the fistula formation-inducing material, a tissue fistula is formed around the fistula formation-inducing material. At this time, if a factor with a physiological function such as endothelial cell growth factor is retained in the fistula formation-inducing material, cells such as endothelial cells can be attached in a state wherein they are preferentially and/or selectively exposed on the luminal surface of the tissue fistula.

Accordingly, in the present invention, after host cells are exposed to a certain degree on the luminal surface of a tissue fistula, these cells increase their number by cell division resulted in a complete cell lining of the luminal surface. With removing the fistula formation-inducing material by some means, an "artificial fistula", wherein the luminal surface is covered with cells, can remain in a living body.

In contrast, according to the findings of the present inventor, in a case of using the silicone rod used in the Sparkes mandril graft of the prior art, fibrin and platelets adhere to the surface of the silicone, fibroblasts preferentially adhere by using this as a scaffold, the fibroblasts actively form fibronectin and these cells then form collagen fibers resulting in the formation of a connective tissue fistula. Consequently, the portion interposed between this connective tissue fistula and the silicone is covered by tissue consisting mainly of collagen fibers and fibroblasts, and fibroblasts synthesize collagen fibers around them, resulted in collagen fiber dominant. Consequently, adherence of endothelial cells is substantially inhibited, and this is presumed to prevent a high-quality "artificial fistula" similar to a blood vessel having endothelial cells on its luminal surface from remaining in a living body.

As is previously described, in the present invention, by using a fistula formation-inducing material, which comprises a solid material (e.g., material having biodegradable polymer as a constituent component) to which, for example, fibrin and/or platelets do not adhere (e.g., having cellular non-adherence and/or antithrombogenicity), tissue fistula formation can be induced that takes advantage of the characteristics of the cell type present at the site where it is used.

According to the present invention, by inserting the fistula formation-inducing material into an abdominal fistula, for example, a tissue fistula can be formed in a living body in the form of an "artificial fistula" that has mesothelial cells, which are present in large numbers in the peritoneal cavity, on its luminal surface. Moreover, when inserted into a constricted portion of the nasolacrimal duct, since there are numerous epithelial cells covering the luminal surface of the nasolacrimal duct at this site, a tissue fistula can be formed in a living body in the form of an "artificial fistula" of which the luminal surface is covered by these cells. Moreover, by inserting it into the cardiac wall or into the spleen or liver, since there are large numbers of endothelial cells that form capillaries present at those sites, a tissue fistula can be formed in a living body in the form of an "artificial fistula" of which the luminal surface is covered by endothelial cells.

Figure 1:
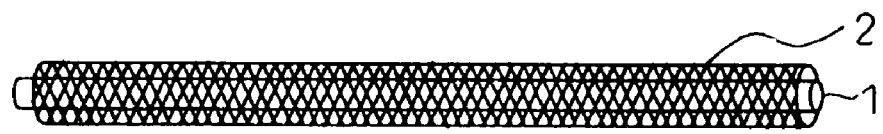
FIG. 1 is a schematic perspective view showing an example of a mandril of the prior art.

In each of the above-mentioned drawings, the meanings of the reference symbols are as follows: 1—silicone rod, 2—mesh, 3—fibroblasts, 4—capillary, 5—collagen fibers.

BEST MODE FOR CARRYING OUT THE INVENTION

The following provides a more detailed explanation of the present invention while referring to the drawings as desired. In the following description, the terms "parts" and "%" used to represent weight ratio are based on weight unless specifically indicated otherwise.

(Fistula Formation-Inducing Material)

There are no particular restrictions on the shape (cross-sectional shape, shape in the longitudinal direction, shape in the circumferential direction and so forth) of the fistula formation-inducing material according to the present invention provided it can be arranged in a living body. Normally, the cross-sectional shape may preferably be circular in view of handling ease and so forth. The cross-sectional shape may also be any other arbitrary shape other than a circle, and a heterogeneous portion may also be present depending on the site of the fistula formation-inducing material. Although this fistula formation-inducing material may not necessarily be hollow, it may have a hollow shape as desired.

Moreover, there are also no particular restrictions on the shape in the longitudinal direction of the fistula formation-inducing material provided it can be arranged in a living body. Although normally it preferably has a nearly uniform diameter in view of handling ease and so forth, it may also have a different shape such as a tapered shape (namely, thickness of the filament body changes moving in the direction of the major axis).

The outer diameter of the fistula formation-inducing material according to the present invention may preferably be 0.1-8 mm, and more preferably 0.5-6 mm, in view of shape retention of the tissue fistula to be formed.

(Fistula Formation Inductivity)

The material according to the present invention is a material that has the property (fistula formation inductivity) of forming "a fistula wherein cells are exposed on at least a portion of the fistula luminal surface" on at least its surface portion. In the present invention, this "fistula formation inductivity" can be measured in, for example, the manner described below.

<Measurement of Fistula Formation Inductivity>

A fistula is formed using a material for which "fistula formation inductivity" is to be measured in compliance with Example 1 described hereinafter.

A section in the circumferential direction of the fistula formed in this manner (preferably having a thickness of about 5 μm) is prepared using a microtome. After staining the cells that compose the inner wall of this section using a staining method that combines a typical staining method like hematoxylin-eosin staining with special staining and so forth capable of staining various types of cells, the cells are observed with an optical microscope (magnification: about 200×). At this time, the length of the luminal surface is measured in at least five arbitrary microscopic fields. This length is designated as a mm. Next, if any cells are present which are exposed on the inner wall, the length of the inner wall is measured at the portion which is covered by those cells, and this is designated as b mm. (Refer to the literature such as Sano Y. ed., Histology Research Method, and William Bloom and Don W. Fawchett, eds., A Textbook of Histology, W. B. Saunders Company, Philadelphia for further details on these section preparation, staining and cell counting procedures.)

In a fistula formed based on the sample of the present invention, the coverage rate (arithmetic mean) by the exposed cells (100×b/a) may preferably be 1% or more. The ratio of the number of non-fibroblasts, such as endothelial cells, mesothelial cells, and epithelial cells, is more preferably 3% or more, and particularly preferably 5% or more.

(Fistula Formation Using a Sparkes Mandril)

When fistula formation is carried out under the same conditions as Example 1 to be described later with the exception of using a Sparkes mandril (material described in the examples of U.S. Pat. No. 3,710,777) instead of the material according to the present invention, the fistula inner wall is formed from scar tissue (fibroblasts+collagen), and the inner wall surface is nearly completely covered by collagen. The coverage rate, by the cells, is 0.1% or less.

(Fibrin and/or Platelet Non-Adherence)

The surface of the fistula formation-inducing material according to the present invention may be a material to which fibrin and/or platelets do not adhere. In the present invention, "fibrin and/or platelet non-adherence" can be measured, for example, in the manner described below.

<Measurement of Fibrin and/or Platelet Non-Adherence>

A material to be measured for fibrin and/or platelet non-adherence formed into the shape of a film (size: about 1×0.5 cm) is immersed in fresh blood contained in a silicone-coated test tube and allowed to stand undisturbed for 3 minutes at 37° C. The sample is then removed from the blood and gently washed with physiological saline to remove substances that do not adhere to the material surface.

This material surface is then observed at an arbitrary location using a scanning electron microscope (SEM) at a magnification of 3000×. In the present invention, adherence of fibrin and/or platelets at less than five locations on a surface measuring 10 μm square is defined as being positive for fibrin and/or platelet non-adherence. At this time, five locations are arbitrarily selected and observed on a surface measuring 10 μm square, and those results are then averaged (arithmetic mean).

Examples of the above-mentioned "fibrin and/or platelet non-adherence" may include cellular non-adherence (namely, the difficulty by which cells adhere to the surface even under conditions wherein cells are cultured in a living body and so forth) and/or antithrombogenicity (the difficulty by which platelets adhere to the surface even under conditions which facilitate the formation of thrombi in a living body and so forth).

(Cellular Non-Adherence)

The surface of the fistula formation-inducing material according to the present invention may be a material that has cellular non-adherence. In the present invention, "cellular non-adherence" can be measured, for example, in the manner described below.

<Measurement of Cellular Non-Adherence>

A cellular non-adherent material in the shape of a film (size: about 1×0.5 cm) is placed in a cell culture dish (Corning, 10 ml cell culture dish) and then cell cultured. Although various cells can be used at this time, typically fibroblasts are preferably selected for the cells. Although ordinary solutions can be used for the cell culture liquid, serum is not added. $1 \times 10^5$ cells/ml are disseminated in the culture liquid, the film is removed on day 3, and then gently washed with physiological saline to remove those cells not attached to the material surface.

The sample surface is then observed with a scanning electron microscope at a magnification of 200-2000×. In the present invention, adherence of less than 50 cells to a surface measuring 100 μm square (namely 100 times the size of a surface measuring 10 μm square) is defined as being positive for cellular non-adherence. At this time, 50 locations are arbitrarily selected and observed on a surface measuring 100 μm square, and those results are then averaged (arithmetic mean).

(Antithrombogenicity)

The surface of the fistula formation-inducing material according to the present invention may be a material that has antithrombogenicity. In the present invention, "antithrombogenicity" can be measured, for example, in the manner described below.

<Measurement of Antithrombogenicity>

The method of measuring antithrombogenicity complies with the method used in "Measurement of Fibrin and/or Platelet Non-Adherence". That is, a sample is prepared which is contacted with blood under the same conditions used in "Measurement of Fibrin and/or Platelet Non-Adherence". The sample is similarly observed at a magnification of 200-2000× with a scanning electron microscope.

During the course of observation, adherence of a fibrin network incorporating erythrocytes, leukocytes and platelets, etc. at less than 50 locations on a surface measuring 100 μm square is defined as being positive for antithrombogenicity. At this time, 50 locations are arbitrarily selected and observed on a surface measuring 100 μm square, and those results are then averaged (arithmetic mean).

(Solid Material)

There are no particular restrictions on the type, molecular weight, polarity, hydrophilicity/hydrophobicity or other physical properties of the material provided it can be maintained for a predetermined time period in the solid state (used with the purport of including a gel state) at the temperature inside a living body of an animal (e.g., a human). After having grown endothelial cells on the surface of the fistula formation-inducing material according to the present invention, it is preferable, in view of facilitating removal of the fistula formation-inducing material itself, that at least a portion of the fistula formation-inducing material be biodegradable. Both high molecular weight and low molecular weight materials (e.g., various phospholipids) can be used provided their shape can be maintained for a predetermined period of time. In a case where the fistula formation-inducing material according to the present invention is inserted by some means into a location where cells are present, it is able to function as a solid (also referred to as a "mandril") to allow endothelial cells to grow on the surface.

Examples of polymer materials that can be used in the present invention may include non-biodegradable materials such as synthetic polymers and naturally-occurring polymer materials such as silicone, polyurethane, polypropylene, polyester, polyvinyl alcohol, polymethylmethacrylate, polycarbonate, Nylon and other polyamides, polytetrafluoroethylene (PTFE) and other fluororesins, silk and cellulose, as well as polyglycolic acid, polylactic acid, polylactic acid-polyglycolic acid copolymers, biodegradable (3-hydroxybutyrate) polyester polymers, polydioxane, urokinase, polyethylene glycol, collagen, gelatin, albumin, mucopolysaccharides, fibronectin, alanine, alginic acid, hyaluronic acid, heparin, heparan sulfate, chondroitin sulfate, starch, dextrin, dextran, agarose, pectin, mannan and their derivatives.

In the present invention, the above-mentioned solid material may be composed in a plurality of layers as desired. In this case as well, the surface of the solid material should have the above-mentioned fistula formation-inducing material (having the property for forming a fistula wherein cells are exposed on at least a portion of the fistula luminal surface). In this case, there are no particular restrictions on the means for laminating and/or adhering the material that composes the outer layer (e.g., coating layer) to the material that composes the inner layer. That is, the outer layer is only required to fulfill the function of an outer layer with respect to the inner layer during the time until the fistula formation-inducing material according to the present invention is inserted into a tissue and a fistula is formed around it.

(Gel Material)

The fistula formation-inducing material according to the present invention may also comprise a gel material as desired. In view of biocompatibility, this gel material may preferably be a hydrogel in the wet state. The moisture content of the hydrogel may preferably be 1-99.5% and more preferably 5-80%. This gel material may be a temperature-gelled polymer (TGP) corresponding to a change in temperature (refer to the literature such as Yoshioka, H., Mori, Y., Tsukikawa, S. and Kubota, S., "Thermoreversible gelation on heating and on cooling of an aqueous gelatin-poly(N-isopropylacrylamide) conjugate", Polym. Adv. Tech., 9, 155-158 (1998) for further details on TGP).

In a case where the fistula formation-inducing material according to the present invention comprises a plurality of layers, a gel material (e.g., TGP) can be used for the inner layer (core) and/or outer layer (coating) as desired.

(Biological Origin Material)

A material of biological origin such as cells (endothelial cells, bone marrow cells, etc.) may be contained in the outer layer of the fistula formation-inducing material according to the present invention, as all or a portion of the outer layer, as desired. In this case, if cells of a subject and/or patient himself, into which the fistula formation-inducing material is to be inserted, are used for the material of biological origin, then a fistula is formed wherein the cells are exposed in at least a portion of thereof on the basis of this, enabling so-called "tailor-made medicine".

(Other Characteristics)

The fistula formation-inducing material according to the present invention may also have a porous structure as desired. Having such a porous structure is advantageous since adsorbed factors having a physiological function are gradually released efficiently. The porous structure may be, for example, a disorderly collection of pores or an orderly collection of pores. The following documents, for example, can be referred to with respect to the formation of a tubular structure by penetrating holes serving as an example of such regular pores. "Research on Solid Material Transformation of Polymer Solution Structures", http://www.cheme.Kyoto-u.ac.jp/6koza/research/gel/gel.html (downloaded on Dec. 3, 2001);

"Production of polysiloxane thin films", http://www.jst.go.jp/erato/project/kks_P/sks/sks-08.html (downloaded on Dec. 3, 2001);

(1) Production method of organic silicon thin films, Japanese Patent Application No. 1-131478 (May 26, 1989), Japanese Unexamined Patent Publication No. 2-311579 (Dec. 27, 1990)

(2) Production method of metal-coordinating organic silicon polymers, Japanese Patent Application No. 1-309924 (Nov. 29, 1989), Japanese Unexamined Patent Publication No. 3-168226 (Jul. 22, 1991)

(3) Production method of metal-coordinating organic silicon polymers, Japanese Patent Application No. 1-309926 (Nov. 29, 1989), Japanese Unexamined Patent Publication No. 3-170529 (Jul. 24, 1991)

(4) Organic silica porous body having a controlled pore structure and silica porous body production method, Japanese Patent Application No. 2-414138 (Dec. 10, 1990), Japanese Unexamined Patent Publication No. 4-210227 (Jul. 31, 2002)

(5) Production method of metal oxide thin film, Japanese Patent Application No. 3-68047 (Mar. 7, 1991), Japanese Unexamined Patent Publication No. 4-280802 (Oct. 6, 1992)

(6) Production method of metal oxide thin film, Japanese Patent Application No. 3-183836 (Jun. 27, 1991), Japanese Unexamined Patent Publication No. 5-5041 (Jan. 14, 1993)

(7) K. Sakata and T. Kunitake, Deployment of Organized Molecular Silica—Ceramic Data Book '91 (Industrial Product Technique Association) p. 41-46 (1991)

(8) K. Sakata and T. Kunitake, Synthesis of Organized Molecular Silica, New Ceramics, September issue (1992)

(9) K. Sakata and T. Kunitake, Siloxane Polymer Films with Varied Microstructures, Chemistry Letters, No. 12, p. 2159-2162 (1989)

(10) K. Sakata and T. Kunitake, A Multilayered Ultrathin Film of Siloxane Network, J. Chem. Soc., Chem. Commun., p. 504-505 (1990)

The fistula formation-inducing material according to the present invention, in consideration of ease of handling during insertion, preferably has rigidity in the dry state (e.g., in the state before being inserted into a living body) and/or flexibility and bendability in the wet state (e.g., in the state after being inserting into a living body). These characteristics can be easily realized by using, for example, the above-mentioned "gel material".

An arbitrary drying method can be used to achieve the above-mentioned dry state. Examples of such drying method may include a freeze drying treatment and an air drying (blow drying) treatment.

The fistula formation-inducing material according to the present invention (e.g., polymer) may be insolubilized and/or crosslinked as desired to impart suitable rigidity. This insolubilization and/or crosslinking may be carried out with heat, an electron beam, gamma rays, ultraviolet rays, pressure, drying, entwining or other physical energy. Alternatively, it may be carried out with a chemical crosslinking agent such as formaldehyde, glutaraldehyde, polyepoxy compounds, dialdehyde starch or hexamethylene diisocyanate.

Moreover, the above-mentioned fistula formation-inducing material can also be insolubilized by putting into a coordinated bonded state with a metal such as zinc, magnesium, iron or aluminum.

(Biodegradable Material)

In the present invention, a material having biodegradability may preferably be used for the fistula formation-inducing material. This biodegradability may preferably be that to the degree to which the material is degraded and absorbed in a living body within 12-24 months (and more preferably within 6 months and particularly preferably within 3 months).

Biodegradability at this time can be measured, for example, in the manner described below.

<Measurement of Biodegradability>

With the sample for which biodegradability is to be measured in the form of plates measuring 10×5 mm, 10 such plates are respectively inserted into the subcutaneous tissue of five rats (e.g., Wistar rats) (on the backs of the rats at a depth beneath the skin of about 5 mm). One of the above-mentioned samples each is sequentially sampled from a single rat at 1 day, 3 days, 7 days, 1 month, 2 months, 3 months, 6 months and 12 months after the start of the experiment, prepared into sections for light microscopy along with the surrounding tissue, and then stained and then observation with a light microscope (magnification: 100×).

In the present invention, the case of the sample completely disappearing after 12 months (namely, the time for complete disappearance is within 12 months) is defined as having biodegradability. This time for complete disappearance may preferably be within 6 months (and particularly preferably within 3 months).

(Specific Biodegradable Materials)

There are no particular restrictions on biodegradable materials that can be used in the present invention provided they have the above-mentioned biodegradability. Preferable examples of biodegradable materials may include materials having as constituent elements at least one selected from the group consisting of polyglycolic acid, polylactic acid, polylactic acid-polyglycolic acid copolymers, biodegradable (3-hydroxylburate-4-hydroxylbutyrate) polyester polymers, polyethylene glycol, polydioxane, collagen, gelatin, albumin, fibrin, chitosan, chitin, fibroin, cellulose, mucopolysaccharides, fibronectin, laminin, alginic acid, hyaluronic acid, chondroitin sulfate, polyamino acid, dextran, agarose, pectin, mannan and their derivatives. These materials are easy to use since they have already been proven as medical materials and so forth. However, other arbitrary materials can also be used provided they have the characteristic of being degraded and absorbed within 12 months (preferably within 6 months and more preferably within 3 months) after being implanted in a living body, and are substantially free of toxicity to a living body.

(Example of Production Method)

The fistula formation-inducing material according to the present invention can be formed in, for example, the manner described below.

Equal amounts of hyaluronic acid, protamine sulfate, sodium heparin and polyethylene glycol having a molecular weight of 6000 are mixed to prepare a gel material, and when this is extruded with a syringe in an ethanol solution of aluminum chloride (or a 100% alcohol solution of a 3% epoxy compound, EX-313, Nagase Chemical, Osaka), the above-mentioned gel solidifies in the form of a filament. This is then freeze-dried and then sterilized with ethylene oxide gas, ultraviolet light or electron beam to obtain the fistula formation-inducing material according to the present invention.

(Mechanism for Tissue Fistula Formation)

The fistula formation-inducing material according to the present invention does not substantially cause non-biodegradable cellular activity or its subsequent incomplete the tissue formation as is observed with the silicone used in conventional Sparkes mandril grafts. This mechanism is presumed to be as described below based on findings of the present inventor.

As the fistula formation-inducing material according to the present invention has fibrin and/or platelet non-adherence (e.g., cellular non-adherence and/or antithrombogenicity) at least on a portion of its surface, even in a case where having been arranged in a living body, there is little adherence of fibroblasts and other cells. In addition, even if bleeding occurs caused by the insertion procedure, platelet formation and/or precipitation of fibrin attached to the fistula formation-inducing material can be reduced at the site. Consequently, the adherence of fibroblasts and other cells between the cellular tissue originally present and the fistula formation-inducing material is inhibited, thereby making it possible to secure space that enables division, reproduction and migration of cells in the interstices between the original cellular tissue and fistula formation-inducing material as well as circulation of body fluids or cell culture liquid required for the tissue formation. In this manner, liquid components are always present and body liquids are able to circulate among the cells in this space. Consequently, it is presumed that the present invention is able to maintain a suitable environment for the growth of endothelial cells, serous membrane cells and other cells having the property of being able to cover the luminal surface of the fistula at this portion.

Moreover, if a substance which is absorbed and degraded in a living body, and has an ability to fix or retain heparin or various cell growth factors, is used for this fistula formation-inducing material, cells rapidly gather around the periphery of the fistula formation-inducing material, and the formation of a tissue fistula wherein a surface coating is obtained by exposure of the cells is accelerated. As a fistula can be formed by artificially gathering different types of cells as a result of changing the type of cell growth factor or cytokine used at this time, various new types of tissue fistula can be formed artificially depending on the contrivances made.

Accordingly, the use of the fistula formation-inducing material according to the present invention makes it possible to form various types of tissue fistula if cells are used such as stem cells having the potential to differentiate in various directions or cells having the potential to form numerous cell growth factors (Noishiki, Y., Tomizawa, Y., Yamane, Y. and Matsumoto, A.: Autocrine angiogenic vascular prosthesis with bone marrow transplantation, Nature Medicine, 2: 90-93, 1996).

(Mode of Use)

There are no particular restrictions on the means for arranging the fistula formation-inducing material according to the present invention in a living body. In a case where the fistula formation-inducing material according to the present invention has a certain degree of rigidity, for example, the fistula formation-inducing material can be inserted into a living body as is. On the other hand, by arranging the fistula formation-inducing material within a tubular member (tunnel tube) for inserting the fistula formation-inducing material at a location where cells are present as desired and then extracting the tubular member immediately thereafter, the fistula formation-inducing material may be left in a living body. That is, by inserting the fistula formation-inducing material according to the present invention at a location where cells are present, cells such as endothelial cells that have the property of covering the fistula luminal surface are exposed on the surface of the tissue with which the fistula formation-inducing material makes contact in a living body, and are able to grow to form a tissue fistula.

When arranging the fistula formation-inducing material in a living body, after having arranged the fistula formation-inducing material within a tubular member as described above, the tubular member may be arranged in a living body, or the tubular member may be inserted into body tissue and then inserting the fistula formation-inducing material (mandril) into that tunnel tube. In this case, body tissue can be perforated, using a needle, either by attaching a needle to the end of the mandril or forming the end of the mandril into the shape of a needle, and a portion of the mandril can be implanted in the tissue by separating the mandril from the needle with the mandril still in the tissue.

(Formed Tissue Fistula)

A tissue fistula formed by using the fistula formation-inducing material according to the present invention can be used in various applications, and there are no particular restrictions on those applications. Examples of applications for which this tissue fistula can be used may include an artificial coronary artery creation in the myocardium, an artificial discharge pathway for bile, artificial discharge pathway for cerebrospinal fluid, artificial discharge pathway for aqueous humor, artificial ureter, artificial urinary tract, artificial discharge pathway for ascites, artificial veins, uterine tube reparative auxiliary material, spermatic cord reparative auxiliary material, vascular reparative auxiliary material (e.g., that having an inner diameter of 6 mm or less), nasolacrimal duct reparative auxiliary material, salivary duct reparative auxiliary material, artificial lymph ducts, trachea reparative auxiliary material, tendon sheath reparative auxiliary material, neural tube reparative auxiliary material, and intra-hepatic blood vessel reparative auxiliary material.

(In Vitro Use)

The fistula formation-inducing material according to the present invention can also be used in vitro. A fistula can be formed in vitro by, for example, covering the periphery of this material (e.g., gel) with a tube made of fabric (e.g., Dacron fibers), and causing tissue and/or cells (such as vascular endothelial cells or ureteral endothelial cells) to be entangled in this fabric tube. At this time, by adhering a cell growth factor (e.g., vascular endothelial cell growth factor) to the gel, cells are made to be exposed on the luminal surface and ultimately, the formation of tissue in the shape of a fistula, of which the luminal surface is covered by these cells, can be induced in vitro.

(Sparkes Mandril Graft)

The following provides a detailed explanation of the method of vessel formation using a Sparkes mandril graft of the prior art for comparison with an actual embodiment of use of the present invention to be described later.

Figure 2:
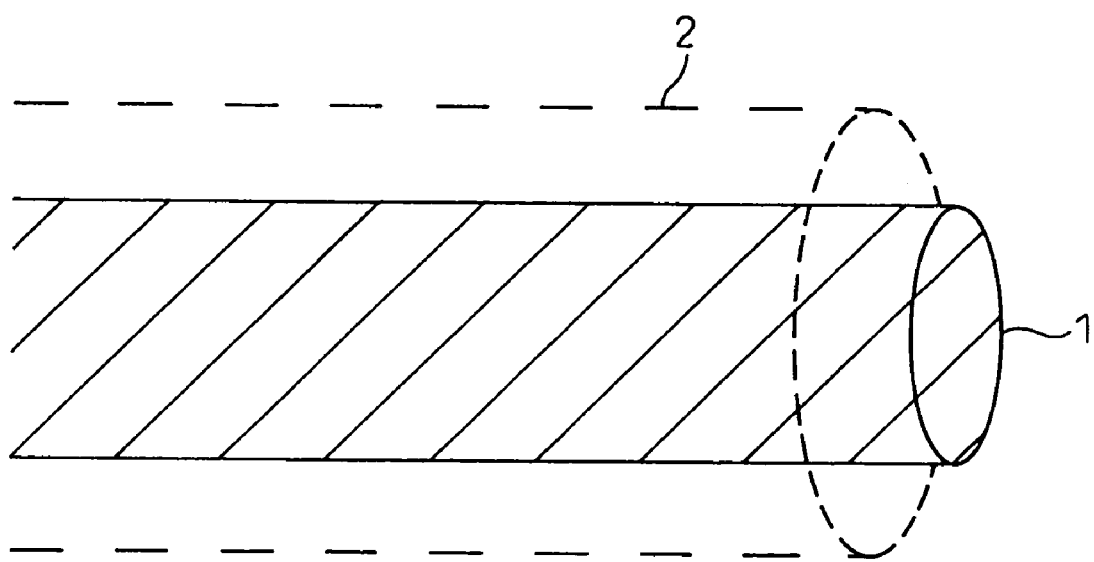
FIG. 2 is an enlarged view of FIG. 1.

With reference to FIG. 1, which is a schematic perspective view showing an embodiment of the constitution of a Sparkes mandril graft, the mandril graft is composed by arranging a mesh (made of "Dacron" fibers and so forth) around the periphery of a silicon rod. FIG. 2 is an enlarged view of FIG. 1.

Figure 3:
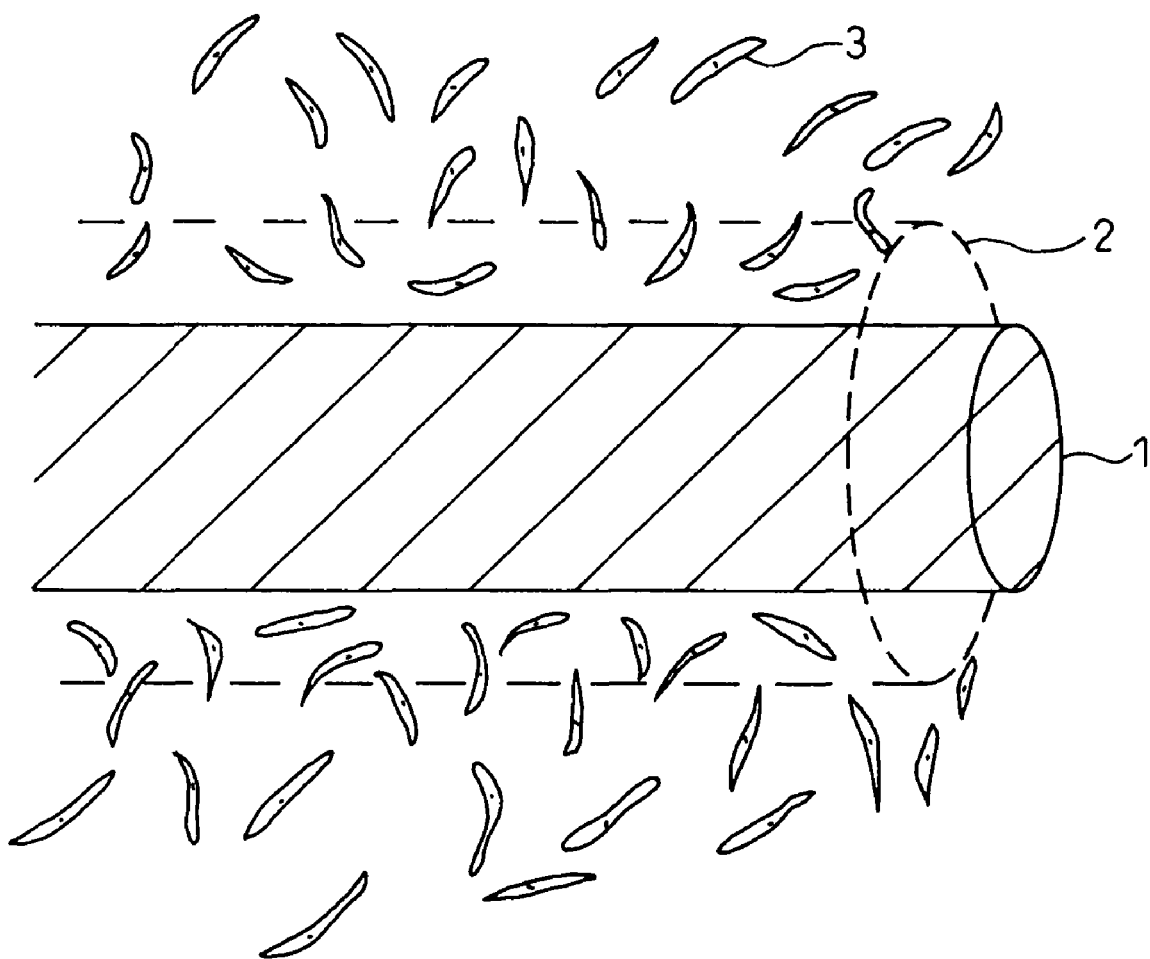
FIG. 3 is a schematic perspective view showing the state wherein fibroblasts infiltrate into the area near the mandril of FIG. 1.

When a blood vessel is formed using this graft by inserting it into a living body (subcutaneous tissue), as shown in FIG. 3, fibroblasts 3 infiltrate the graft from the external periphery, and reach the surface of silicon rod 1 by passing through interstices in mesh 2.

Figure 4:
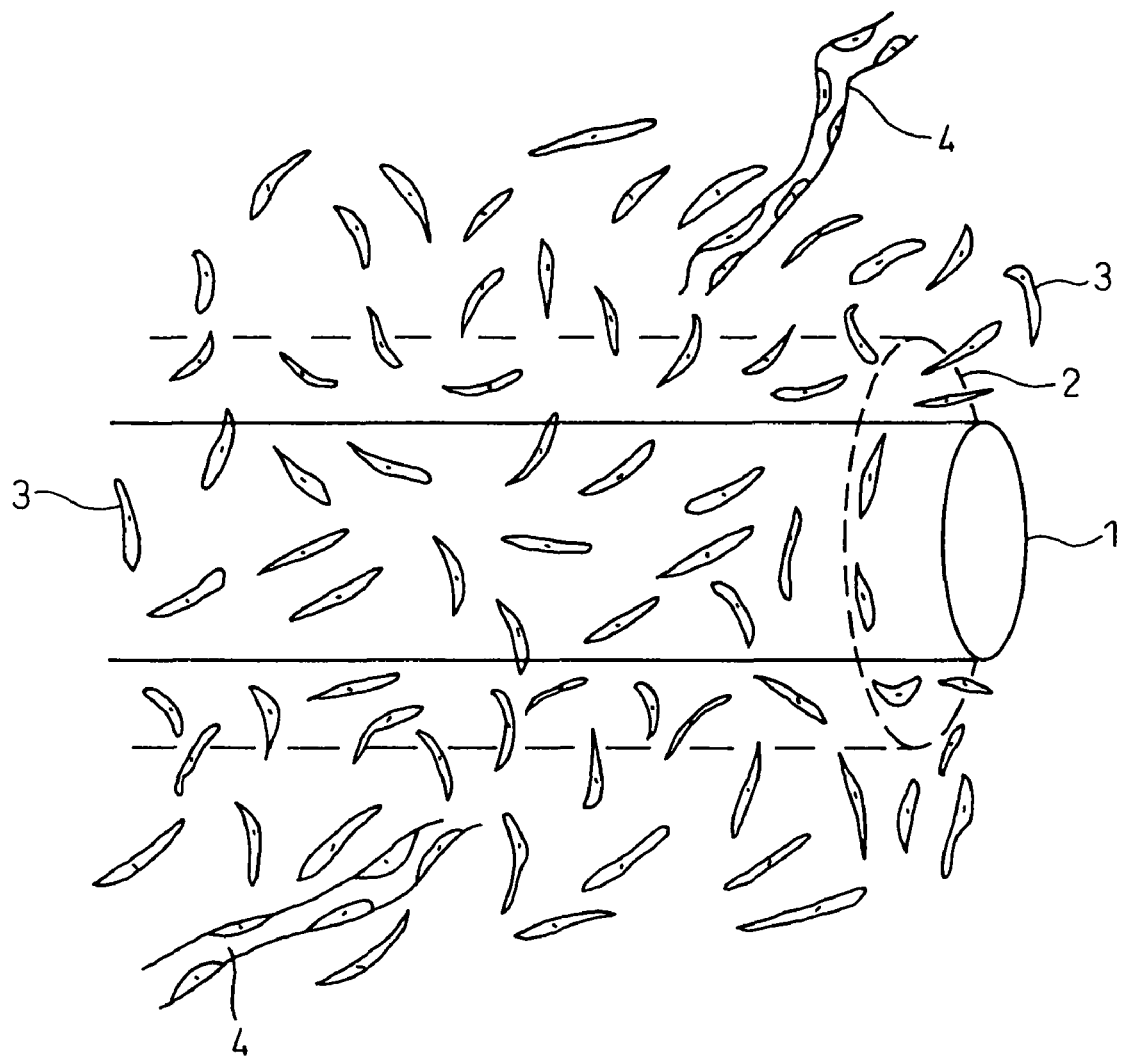
FIG. 4 is a schematic perspective view showing the state wherein fibroblasts infiltrate the interstices between the rod and mesh of the mandril of FIG. 1.

Moreover, after a certain period of time has elapsed (about 10 days), as shown in FIG. 4, fibroblasts 3 infiltrate into the area near a silicon rod 1 so as to surround it and also infiltrate between the interstices of mesh 2 and silicon rod 1 on the inside of mesh 2. The invading fibroblasts 3 multiply and completely fill in mesh 2. Although several capillaries 4 also infiltrate into the graft in order to supply nutrients to these fibroblasts 3, as this collagen fiber rich connective tissue is not active tissue (namely, does not have movement or consume energy in the manner of muscle), the number of ingrowing capillaries 4 is not that large. Although several of the capillaries 4 have the potential to pass through interstices in mesh 2 and reach the periphery of silicon rod 1, as the silicon rod is not antithrombogenic and does not induce endothelial cells, the luminal surface of the tissue fistula that surrounds the silicon rod at that location is not accessible to endothelial cells and endothelial cells do not appear.

Figure 5:
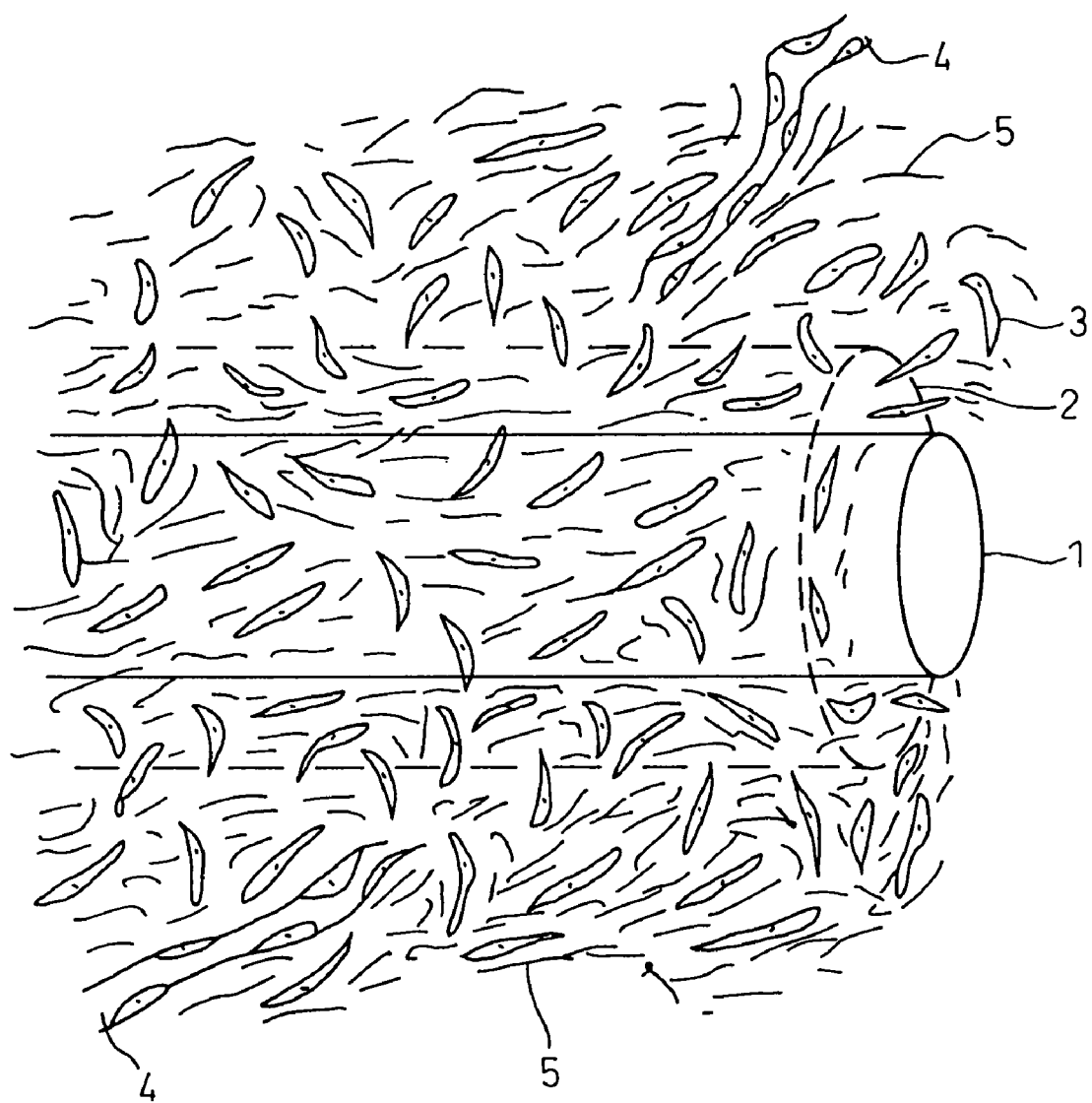
FIG. 5 is a schematic perspective view showing the state wherein fibroblasts that have infiltrated into the area near the mandril form connective tissue by forming collagen fibers.

As time continues to elapse, as shown in FIG. 5, the invading fibroblasts 3 multiply further and, together with increasing in number, an infinite number of collagen fibers are formed in the vicinity of these cells (which is beneficial for their survival). As a result, rugged, fibrous connective tissue is formed thereabout.

At this time, as endothelial cells and various other cells that form the luminal surface of an ordinary fistula organ or fistula tissue are unable to adhere to the silicon rod 1, the silicon rod 1 is surrounded by fibroblasts 3 and collagen fibers, and a certain amount of space is formed between them and silicon rod 1, the interstices of which are filled by tissue fluid. The surface of this connective tissue is composed mainly of collagen fibers, and since fibroblasts near their surface always form collagen fibers around the fibroblasts, they are normally surrounded by a collagen fiber network. Consequently, they are not directly exposed on the tissue fistula luminal surface that surrounds the silicon rod. Although it is possible for capillaries to approach this connective tissue, as the silicon rod is not antithrombogenic and does not induce endothelial cells, endothelial cells do not approach the surface of this connective tissue.

Figure 6:
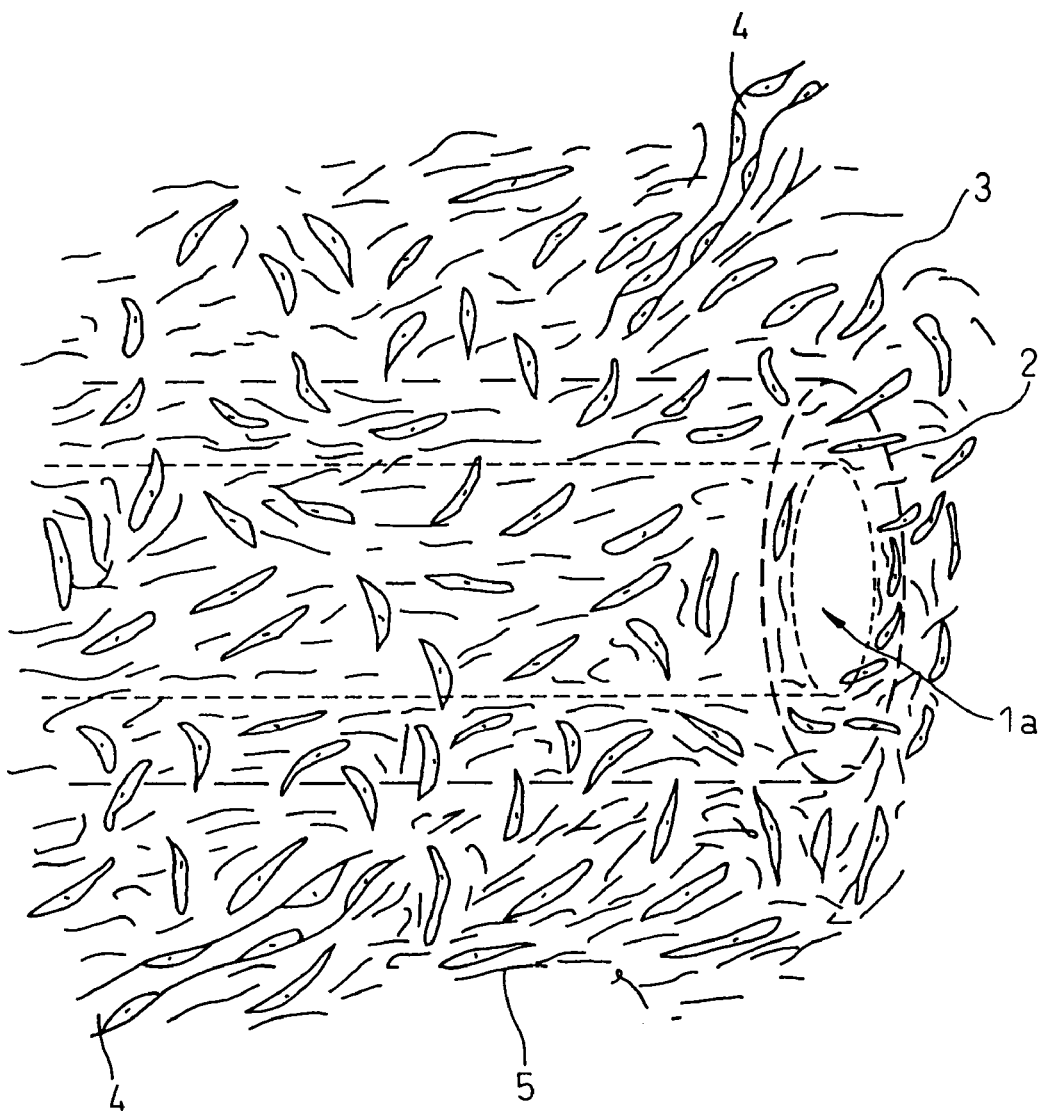
FIG. 6 is a schematic perspective view showing the state wherein the rod has been extracted from the state shown in FIG. 5.

As shown in FIG. 6, after extracting silicon rod 1, a fistula 1a of connective tissue is formed in the state of having used mesh 2 as a framework, as a result of the extraction. According to the concept of Sparkes, this fistula 1a can be used as an artificial blood vessel. This fistula 1a is a tube of connective tissue formed by fibroblasts 3 and collagen fibers 5. Although this connective tissue contains an extremely small number of capillaries 4, hardly any of these capillaries 4 are exposed on the inner wall of fistula 1a. The inner wall (fistula luminal surface) of fistula 1a comprises fibroblasts 3 and collagen fibers 5.

Under such circumstances in a living body, as is previously described related to the Sparkes Mandril Graft, the tissue formation in a living body does not proceed as would be expected, and the mandril must be inserted in a living body for a period of at least three months in order to obtain reliable tissue formation. In addition, adherence of cells to the fibers is poor even in a case where it was inserted into a living body for a long period of time in this manner and, as the tissue formation tends to be incomplete at the portion which contacts with the silicon filament on the inside of the Dacron fabric in particular, this has been reported to be unable to fulfill the function of an artificial blood vessel (Noishiki, Y. and Yamane, Y.: Problems with Sparkes Mandril Grafts, Zinko Zoki, 7(3), 514-517, 1978).

(Embodiment of the Fistula Formation-Inducing Material According to the Present Invention)

Figure 7:
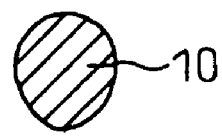
FIG. 7 is a schematic cross-sectional view showing an example of a basic embodiment of the fistula formation-inducing material according to the present invention.

The following indicates an embodiment wherein the present invention can be used. FIG. 7 is a schematic cross-sectional view showing a basic embodiment of the fistula formation-inducing material according to the present invention. This embodiment of the fistula formation-inducing material comprises solid material cylinder 10. The diameter of cylinder 10 of this embodiment may preferably be narrow (e.g., about 2 mm). As is previously described, this cylinder 10 may preferably be a hydrogel or other biodegradable material. When using this cylinder 10 to form an artificial blood vessel, it is extremely preferable that the surface of cylinder 10 has cellular non-adherence and antithrombogenicity. A material other than a biodegradable material (although this is normally premised on it being extracted following fistula formation) may be used for the material that composes this cylinder 10.

The material that composes cylinder 10 may also be a material which is capable of containing or adsorbing various physiologically active substances (such as growth factors and antibiotics), and be able to gradually release the physiologically active substances, as desired.

Figure 8:
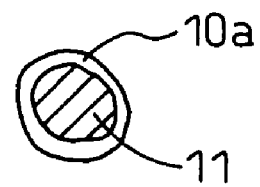
FIG. 8 is a schematic cross-sectional view showing an example of another embodiment of the fistula formation-inducing material according to the present invention.

FIG. 8 shows an embodiment wherein an outer layer 10a is arranged around the periphery of an inner layer (mandril) 11. The same material that composes cylinder 10 of FIG. 7 can be used for the material that composes outer layer 10a. On the other hand, a material other than a biodegradable material may be used for inner layer 11 (although this is normally premised on being extracted following fistula formation). This embodiment is advantageous when enhancing the mechanical strength of outer layer 10a. In addition, inner layer 11 is not necessarily required. In a case where having adequate mechanical strength with outer layer 10a alone (namely, a hollow outer layer 10a alone can be used for the fistula formation-inducing material according to the present invention).

Moreover, in a case of using a biodegradable material for outer layer 10a, it is extremely preferable that the surface of mandril 11 also has cellular non-adhesion and antithromboticity (due to the possibility of the mandril 11 being exposed).

Figure 9:
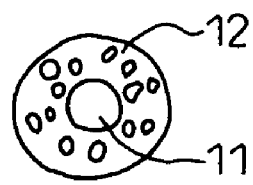
FIG. 9 is a schematic cross-sectional view showing an example of another embodiment of the fistula formation-inducing material according to the present invention.

FIG. 9 shows an embodiment composed of a hollow porous outer layer 12a. This porous outer layer 12a may be made to contain and/or entwine the above-mentioned physiologically active substances, cells or tissue fragments and so forth as desired (for example, these additives can be put into a solution state and then arranged within porous outer layer 12a). Inner layer 11 should be arranged as desired corresponding to the purpose of enhancing mechanical strength and so forth.

(Application to Blood Vessel Formation in the Cardiac Wall)

Figure 10:
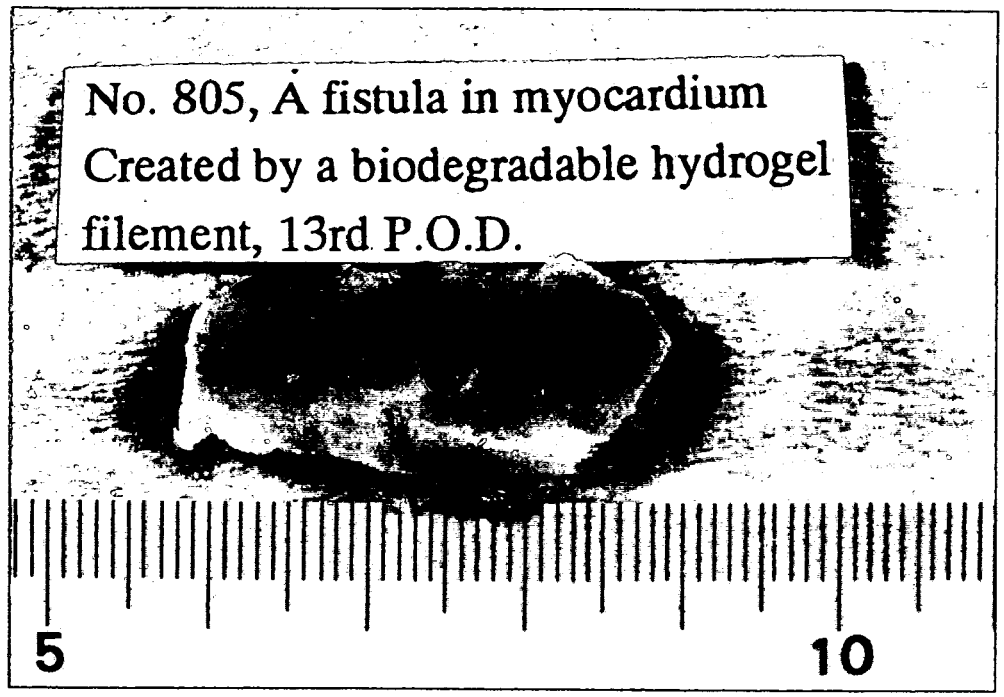
FIG. 10 is a cross-sectional photograph showing an example of a fistula formed in the cardiac wall of a dog using the fistula formation-inducing material according to the present invention.
Figure 11:
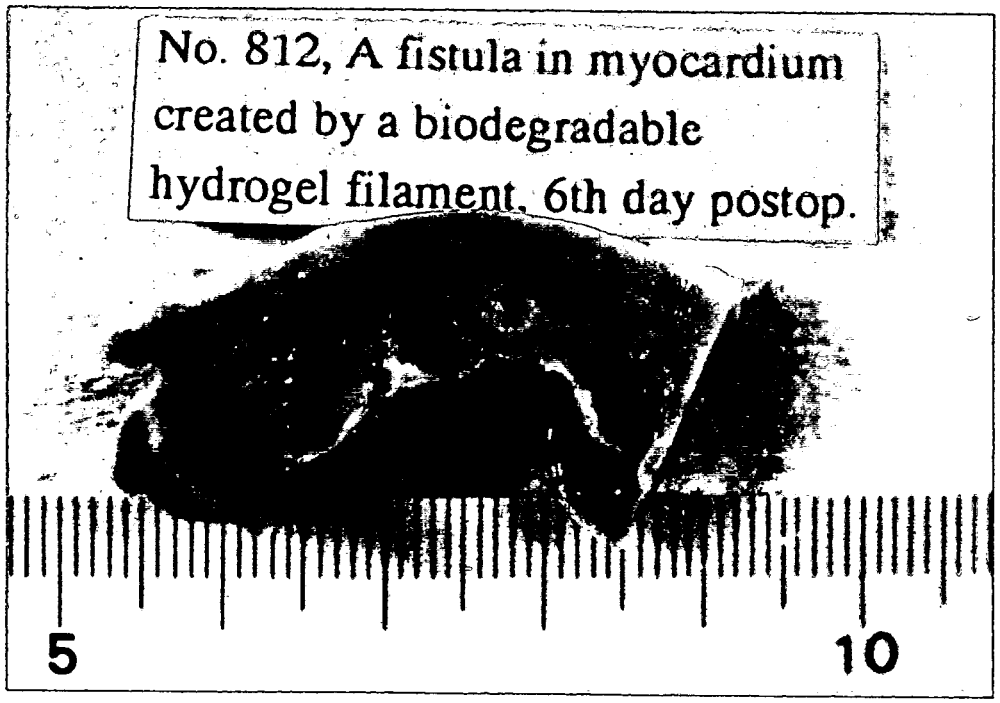
FIG. 11 is a cross-sectional photograph showing another example of a fistula formed in the cardiac wall of a dog using the fistula formation-inducing material according to the present invention.

The following provides an explanation of a mode wherein the fistula formation-inducing material according to the present invention is inserted into cardiac muscle tissue to form a blood vessel in the cardiac wall. Forming a blood vessel in an ischemic portion of the heart in this manner makes it possible to restore blood flow in patients wherein blood flow cannot be restored surgically or in myocardial infarcted portions which cannot be revived using a catheter. FIGS. 10 and 11 are photographs of the cardiac wall of a heart (dog) wherein a blood vessel has been formed using this technique.

Figure 12:
FIG. 12 is a schematic perspective view showing an example of a basic embodiment of the fistula formation-inducing material according to the present invention.

FIG. 12 shows an example of a fistula formation-inducing material according to the present invention (e.g. gel) that can be preferably used in this embodiment. This material 20 may be in the dry state or wet state. When applied to the heart, the material preferably has a length of about 3-10 cm and thickness of about 1-3 mm in consideration of handling ease.

Figure 13:
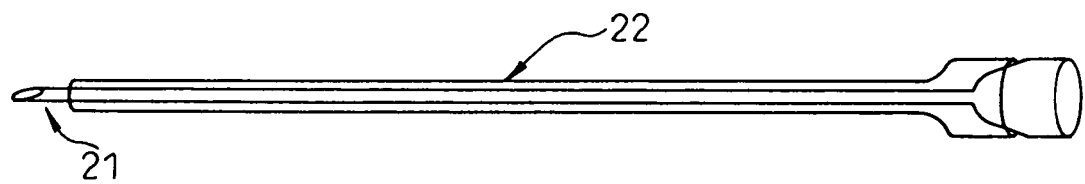
FIG. 13 is a schematic perspective view showing an example of a device for inserting the fistula formation-inducing material according to the present invention into tissue.

FIG. 13 shows a venous indwelling catheter needle for inserting this gel material into a living body. This venous indwelling catheter needle has a duplex structure combining a metal inner needle 21 and a flexible plastic outer catheter 22. After being inserted into a living body, the inner needle is removed and the outer catheter is left in a living body. An interventional approach from a site within the heart may also be used in place of this venous indwelling catheter needle.

Figure 14:
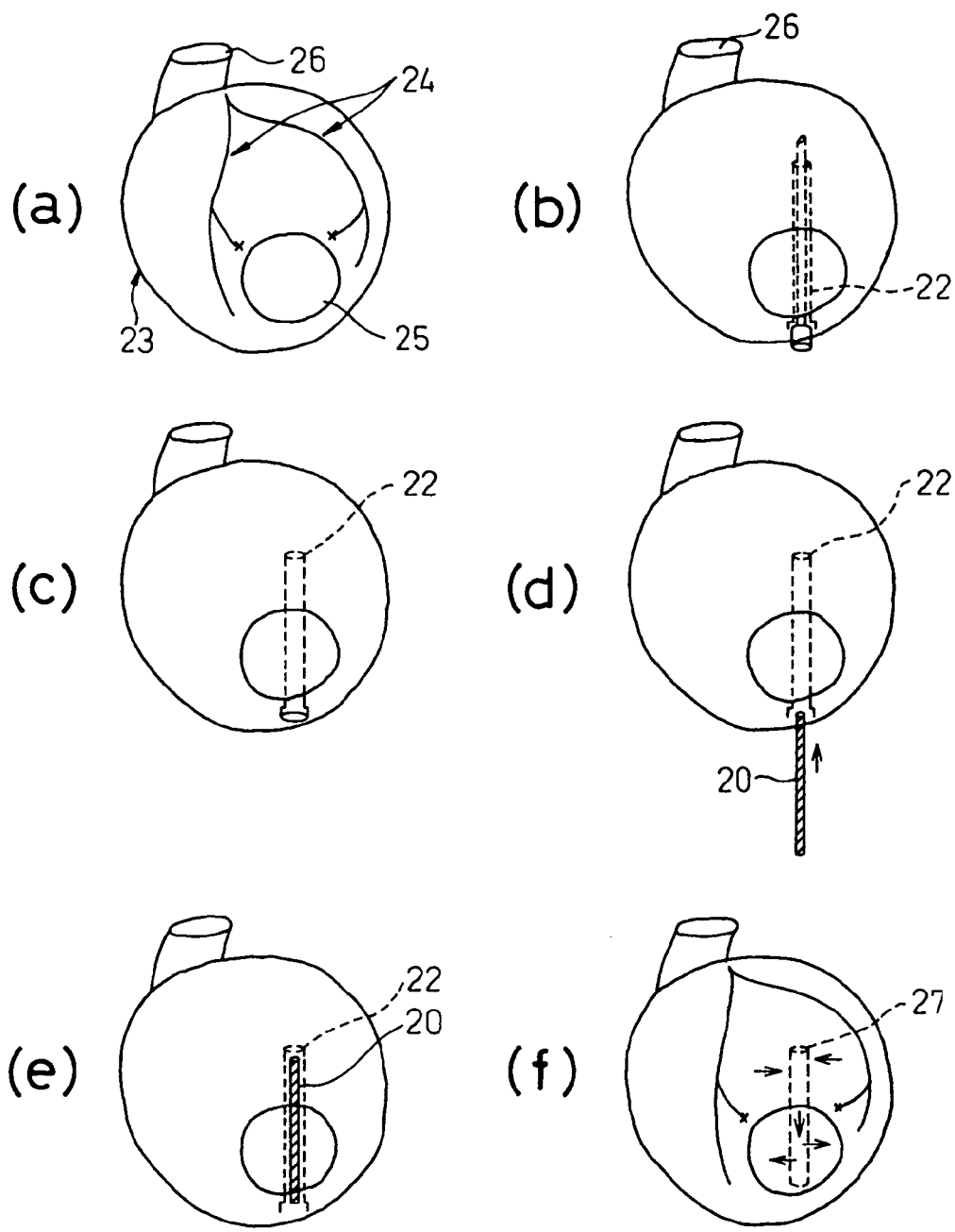
FIGS. 14(a) through 14(f) are schematic perspective views for explaining an example of an embodiment wherein the fistula formation-inducing material according to the present invention is applied to an ischemic portion of the heart.

FIG. 14(a) is a schematic drawing of a heart 23, and shows a cardiac muscle ischemic portion 25 resulting from occlusion of branches of coronary arteries 24 which cannot be repaired surgically. Reference symbol 26 indicates the aorta. In the heart, although the blood flow through large coronary arteries can be maintained by either dilating the vessel using a catheter or by surgically constructing a bypass and so forth, it has previously been impossible to improve an ischemic state if a branch of a narrow coronary artery has become occluded. The method of this embodiment makes it possible to create a new blood vessel in such an ischemic portion 25.

FIG. 14(b) shows the state wherein a venous indwelling catheter needle having a duplex structure as previously described is inserted through this ischemic portion 25 through a healthy portion of the heart, while FIG. 14(c) shows the state wherein the inner needle 21 of the venous indwelling catheter needle has been removed leaving the outer catheter 22 inside the heart. FIG. 14(d) shows the state wherein a gel material 20 is inserted into outer catheter 22. FIG. 14(e) shows the state when gel material 20 is inserted. Subsequently, gel 20 is left in the heart muscle by removing outer catheter 22.

FIG. 14(f) shows the state wherein a new blood vessel has been formed following removal of gel 20 (either by physically removing or by biodegradation). In this manner, blood from the healthy portion of the heart flows to the ischemic portion through the new blood vessel 27.

(Explanation of Myocardial Tissue)

The following provides a supplementary explanation of the characteristics of myocardial tissue itself as a reference for explaining the above-mentioned embodiment of the present invention.

Figure 15:
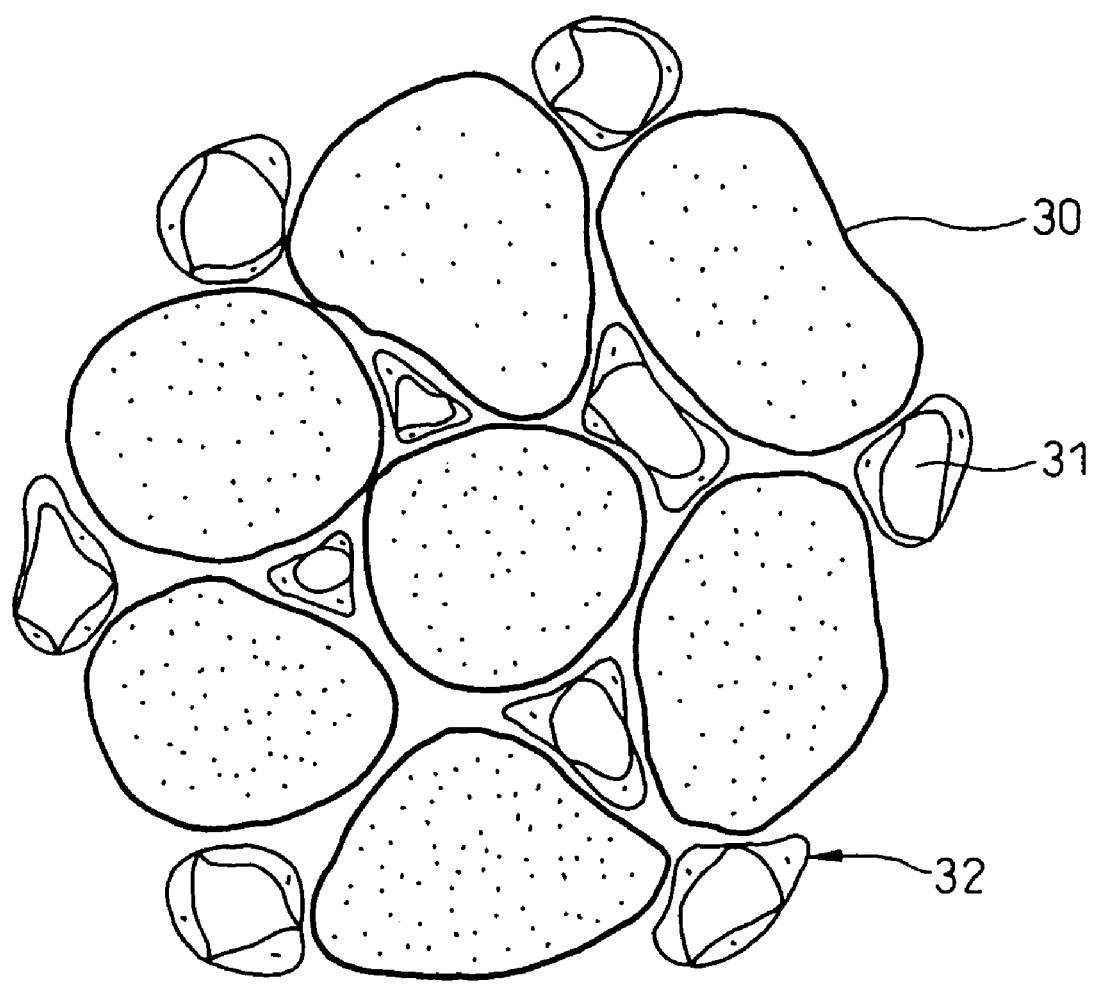
FIG. 15 is a lateral cross-sectional view of an example of heart muscle tissue, i.e. myocardium.

FIG. 15 is a cross-sectional view of myocardial tissue. As shown in this drawing, capillaries 31 are arranged throughout the interstices between myocytes 30 in heart muscle, and myocytes 30 are constantly supplied with ample oxygen and nutrients from these capillaries 31, enabling them to repeatedly contract and relax continuously. These capillaries 31 form a fistula as a result of vascular endothelial cells 32 mutually coming together.

Figure 16:
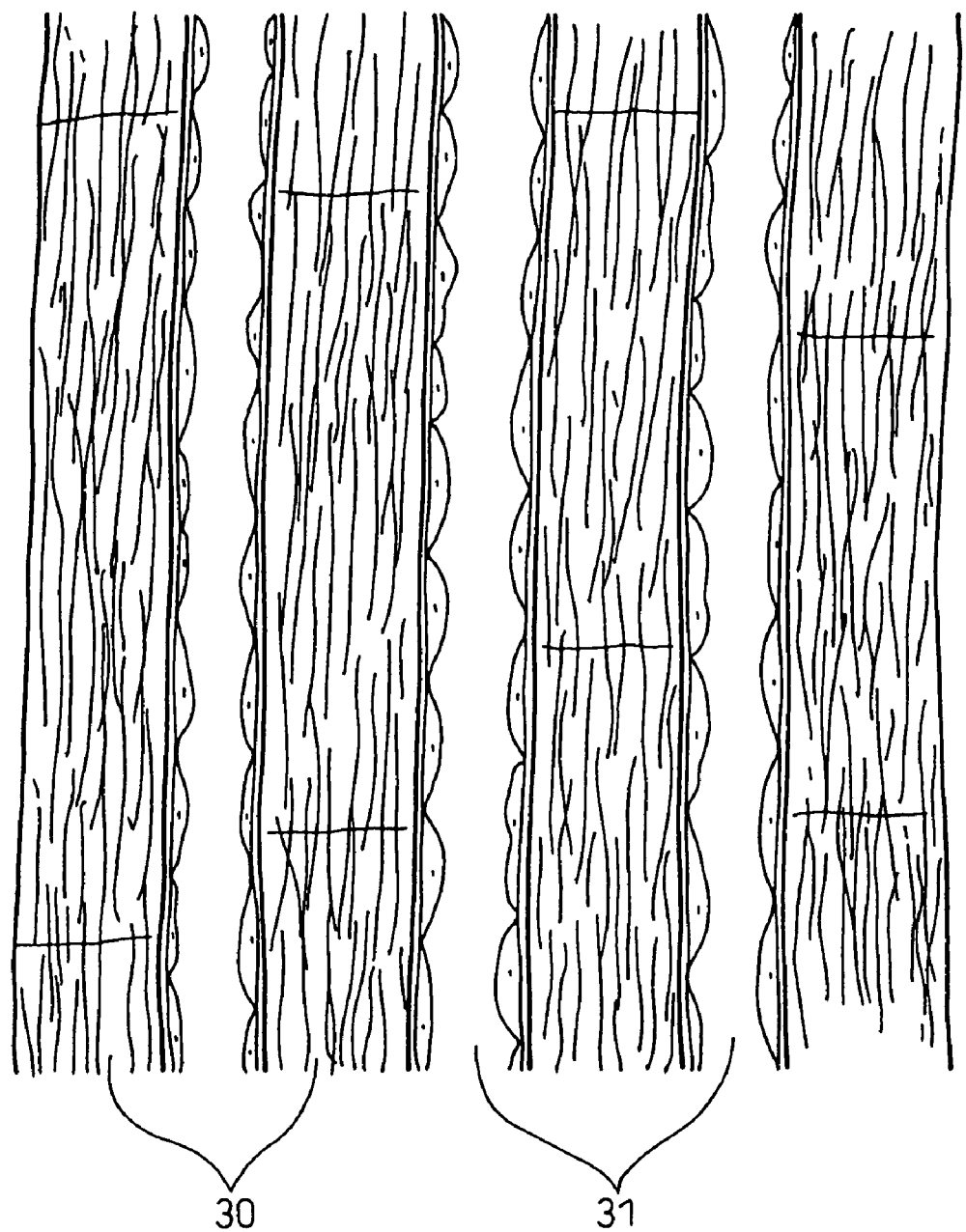
FIG. 16 is a longitudinal cross-sectional view of an example of the myocardium.
Figure 17:
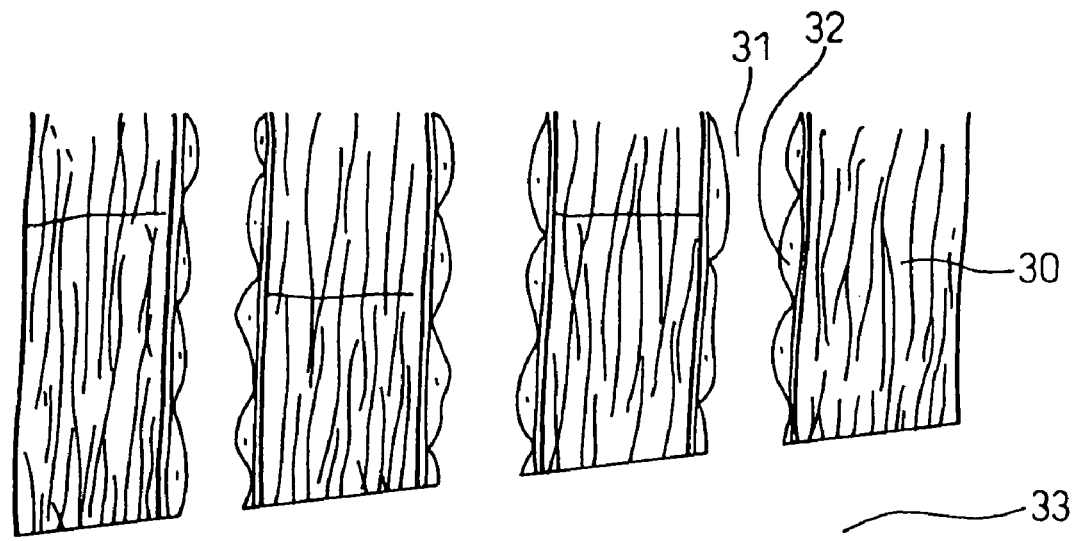
FIG. 17 is a cross-sectional view showing an embodiment wherein the myocardium of FIG. 16 has been pierced to create a fistula.
Figure 17:
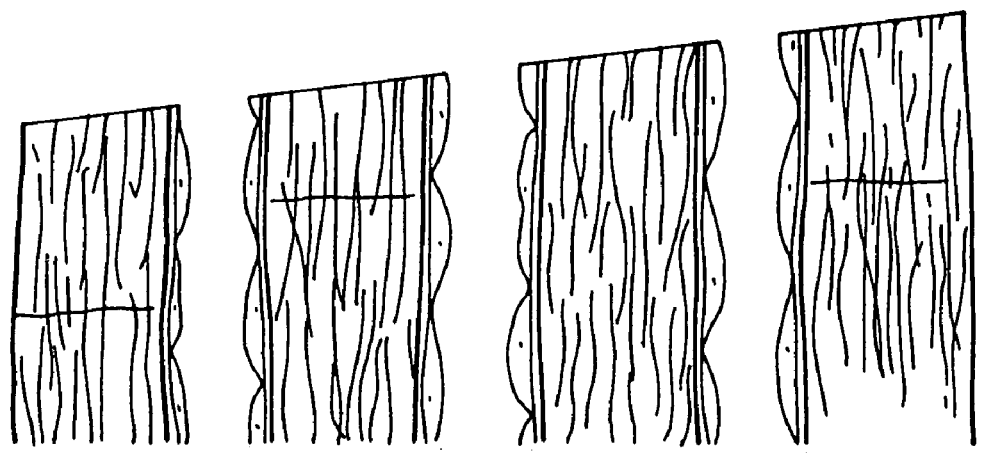

FIG. 16 shows a longitudinal cross-sectional view of myocardial tissue. In this manner, myocytes 30 and capillaries 31 are frequently alternately arranged in parallel in a longitudinal cross-section. As shown in FIG. 17 (showing the severed state), a temporary fistula 33 can be formed by piercing of the myocardial tissue with a sharp needle. At this time, both myocytes 30 and capillaries 31 are severed as shown in this drawing.

In view of causing minimal damage to vascular endothelial cells, it is preferable to mechanically pierce the myocardial tissue with a sharp scalpel (or a venous indwelling catheter or a biopsy needle). Alternatively, although this temporary fistula 33 can be formed using a laser beam. In a case where forming the fistula with a laser beam, as cells surrounding fistula 33 are completely destroyed by the laser heat, the tissue reparative ability of these cells is also nearly completely destroyed, thereby making the use of a laser beam undesirable.

Figure 18:
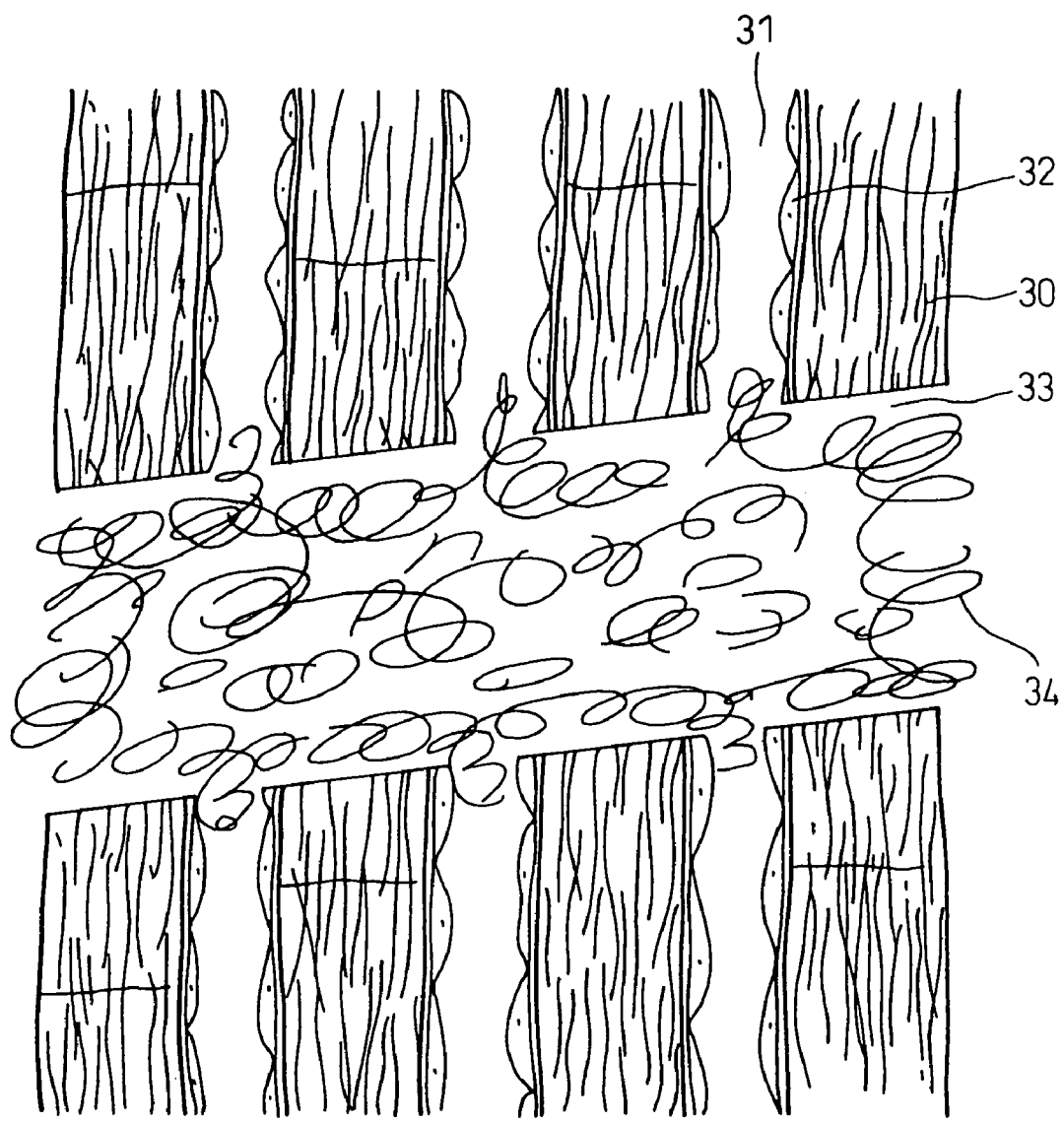
FIG. 18 is a cross-sectional view showing the state wherein thrombus has occupied the lumen of the fistula in the myocardium.

As shown in FIG. 18 (state immediately after perforation), numerous capillaries 31 are destroyed immediately after severing the cardiac muscle layer, hemorrhaging occurs immediately, and this blood soon makes contact with the fistula surface of myocytes 30 and coagulates resulting in the thrombus formation 34. As a result, even if fistula 33 is formed by sharp needle, it is typically occluded by thrombus 34.

Figure 19:
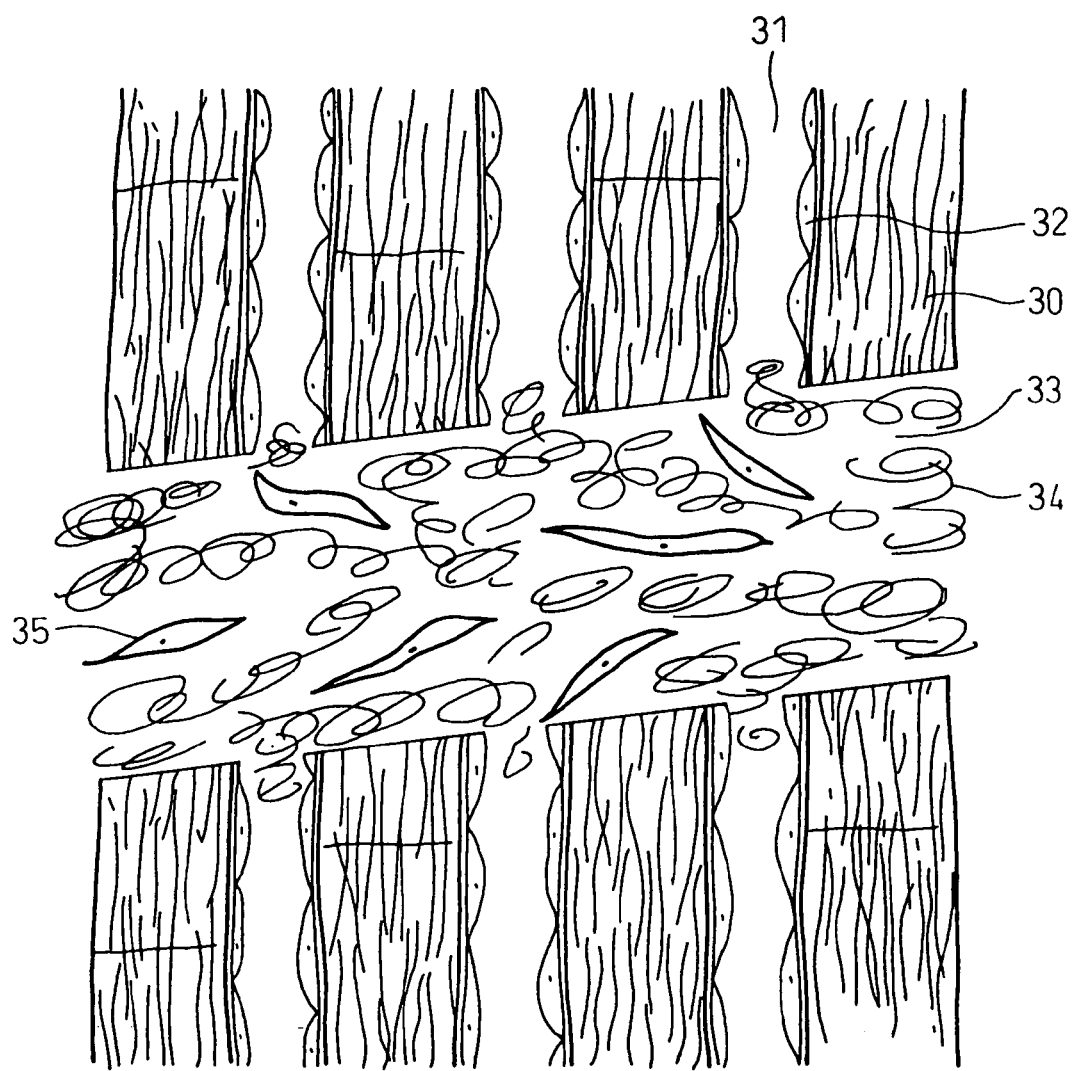
FIG. 19 is a cross-sectional view showing the migration of cells into the thrombus of the fistula in the myocardium of FIG. 18.

As shown in FIG. 19 (change following thrombus formation), migrating cells 35 migrate into the thrombus tissue from the periphery after 2-3 days. The majority of these migrating cells 35 are vascular endothelial cells 32 (which are present in the immediate vicinity). The endothelial cells 32 that have appeared in the thrombus change to more primitive, lower order cells in order to function advantageously for tissue repair (and this phenomenon is referred to as "dedifferentiation"). In a case where endothelial cells 32 are unable to fulfill their inherent function of coating the fistula 33 in this manner, they are mobilized for tissue repair by changing into fibroblasts in the same manner as various cells (including mature cells) as a result of this dedifferentiation phenomenon.

Figure 20:
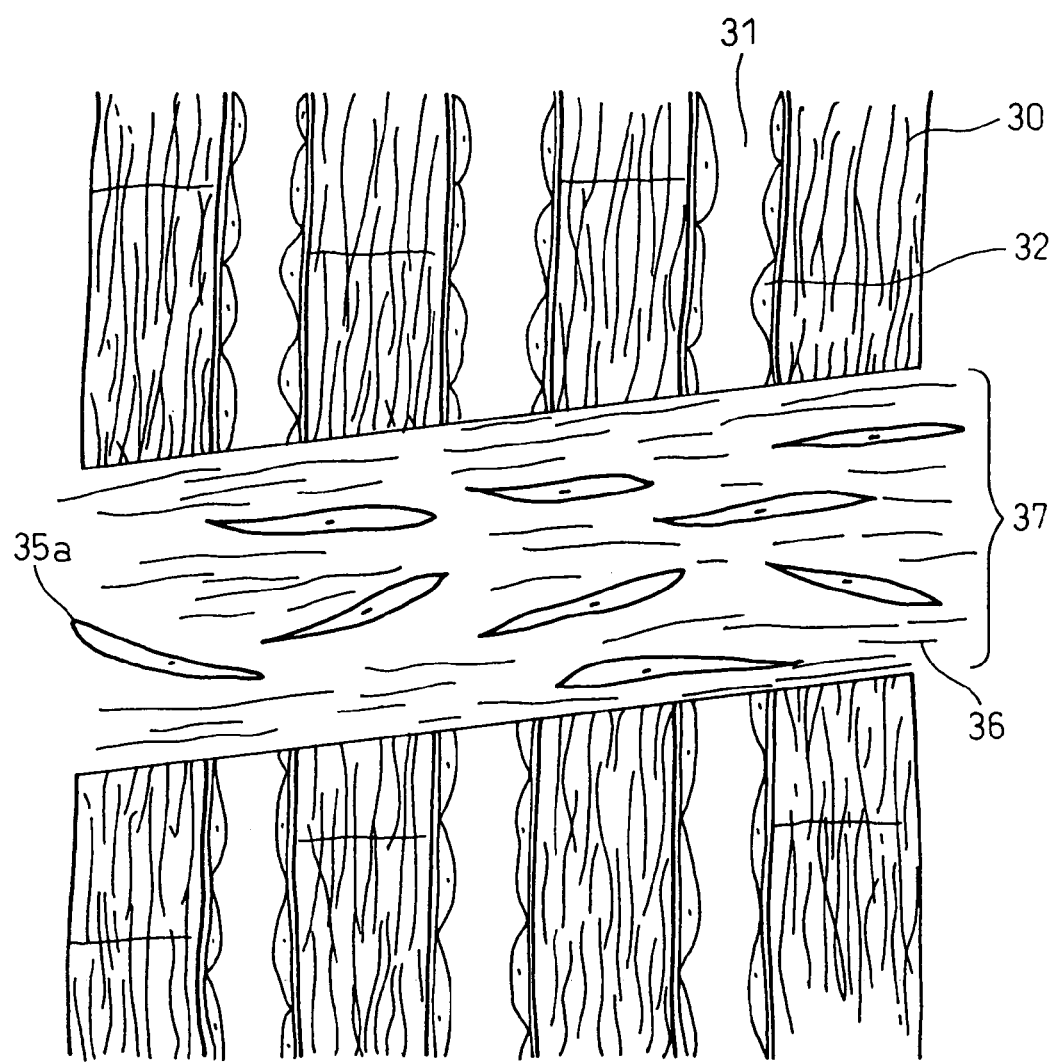
FIG. 20 is a cross-sectional view showing the final state of thrombus repair into a scar tissue.

As shown in FIG. 20 (final state of tissue repair by scar), cells 35, including fibroblasts formed by dedifferentiation phenomenon and the very small number of fibroblasts which are originally present in the vicinity, migrate into the thrombus and proliferate by cell division. At the same time, while gradually forming collagen fibers 36 around their periphery, the fibrin network that formed the thrombus is dissolved by fibrinolysis, ultimately resulting in fibrous connective tissue consisting of fibroblasts 35a and a large volume of collagen fibers 36. Several months later, the number of fibroblasts 35a decreases resulting in scar tissue 37 consisting mainly of collagen fibers.

The formation of this scar tissue 37 has been reported in nearly all results of clinical cases and animal studies involving perforation with a laser beam, and there are no cases wherein the thickness of the opening itself formed by perforation is maintained (Gassler N. Wintzerito, stubbe H M, Wullbrand A. Helm chem. U. Transmyocardial laser revascularization, Histological features in human nonxespouder myocardium, Circulation 1997, Jan. 21: 95(2)371-5).

(Example of Using Material of Present Invention)

Figure 21:
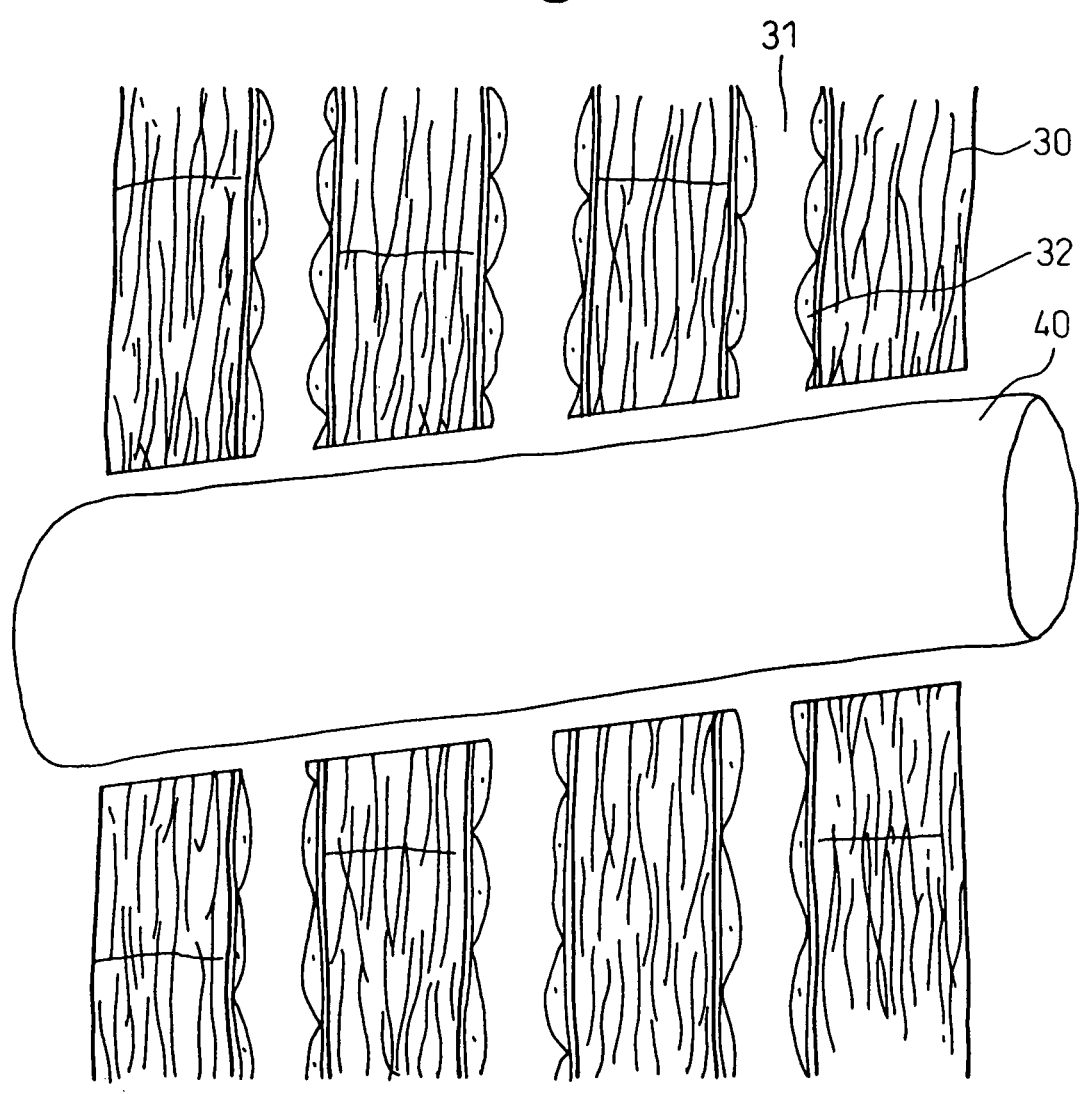
FIG. 21 is a cross-sectional view showing the state wherein the fistula formation-inducing material according to the present invention has been inserted into a fistula in the myocardium.

The following provides a detailed explanation of an example of using the fistula formation-inducing material according to the present invention. In FIG. 21 (state during piercing), while or immediately after the piercing as shown in FIG. 17, the fistula formation-inducing material according to the present invention (in this example, a gel) 40 is inserted into the fistula and the space is occupied by the gel 40.

Figure 22:
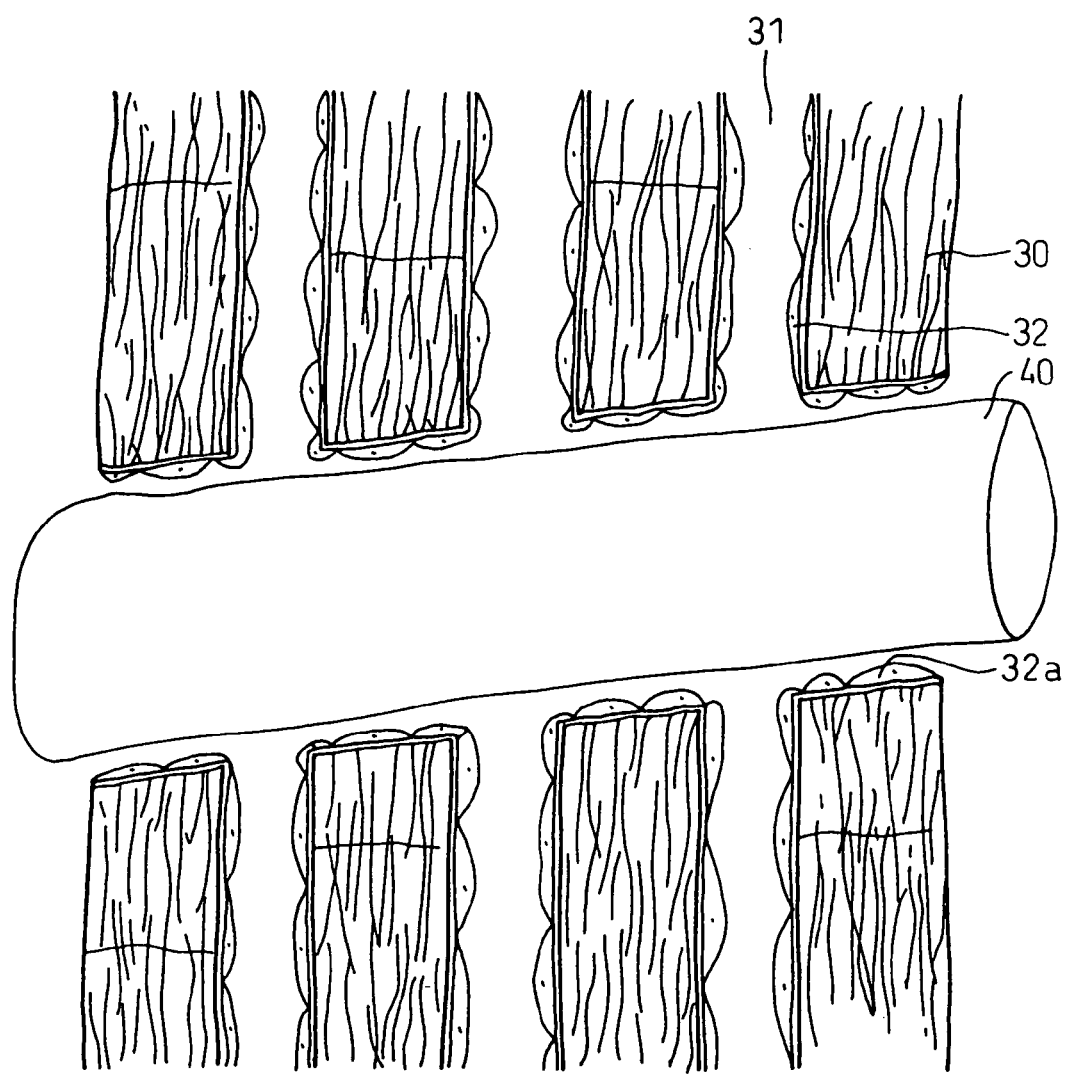
FIG. 22 is a cross-sectional view showing the state of tissue repair at the portion on the luminal surface of the fistula of FIG. 21 where the fistula formation-inducing material has been inserted.

In FIG. 22 (tissue repair following gel insertion), as the gel 40 is present in the space formed by perforation, thrombus is unable to occupy this space (and therefore, the patency of the fistula formed by the piercing is maintained). During this time, endothelial cells migrate for tissue repair from the numerous cut edges of the destroyed capillary blood vessels. Endothelial cells are capable of migrating, proliferating and so forth on the luminal surface. The cells at this time are the above-mentioned endothelial cells 32. Endothelial cells 32 tentatively begin to migrate from the respective cut ends of capillaries 31, and undergo repeated cell division, appearing at locations that have suffered damage.

Since the gel 40 of the present invention has antithrombogenicity (or cellular non-adherence), endothelial cells 32 do not adhere to the surface of gel 40, and become endothelial cells 32 that cover the luminal surfaces of the fistula, i.e., on the myocardial cells. At this time, since endothelial cells 32 fulfill their inherent function of covering the luminal surface of a blood vessel, dedifferentiation does not occur, as they are facing a fresh blood stream, thereby not causing fibroblasts to be formed from endothelial cells 32 (and even if endothelial cells 32 do undergo dedifferentiation, this represents only a very small number of cells). Moreover, although the periphery of the gel 40 is filled with blood, as the gel 40 normally has antithrombogenicity (or cellular non-adherence), there is no coagulation of blood and the fluidity of the fresh blood flow is maintained.

Figure 23:
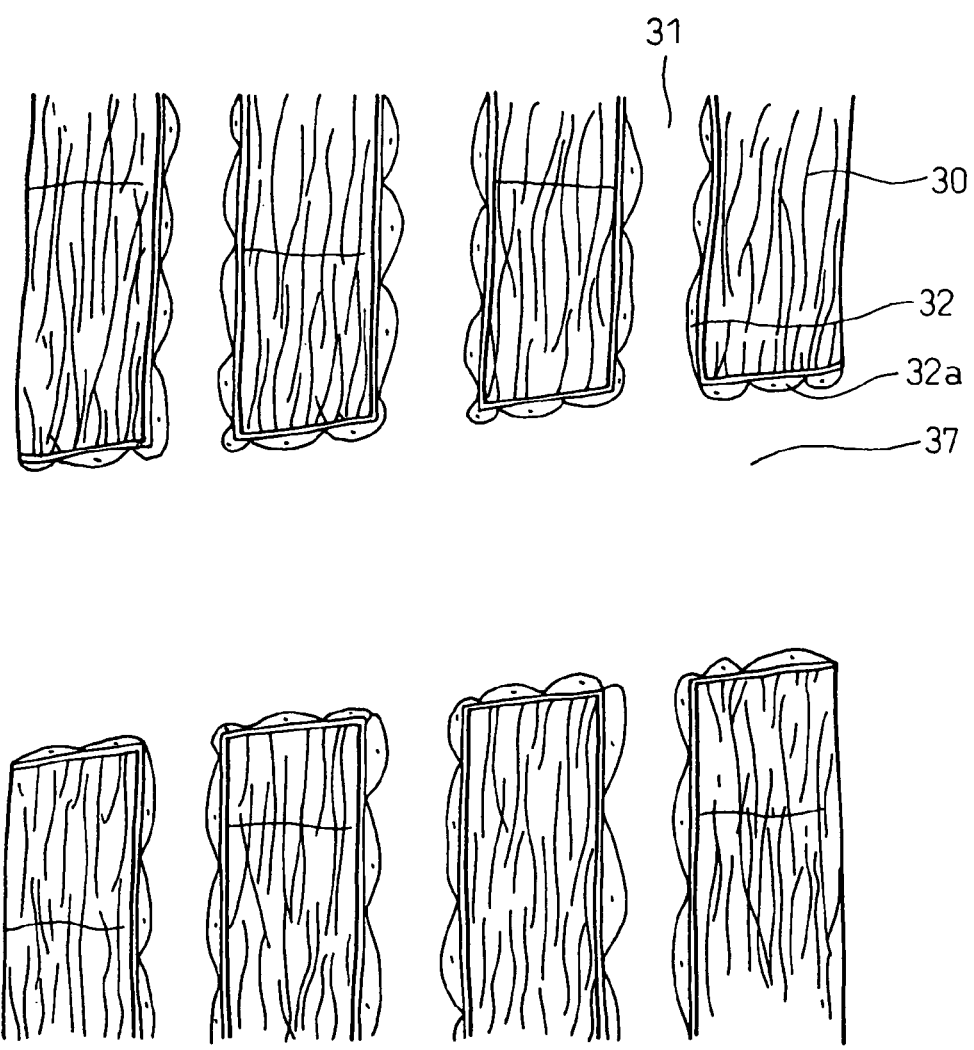
FIG. 23 is a cross-sectional view showing the state following elimination of the fistula formation-inducing material at the portion where the material is inserted. The luminal surface is completely lined with endothelial cells, resulted in creation of a new blood vessel.

Coating by endothelial cells 32a as described above is observed about three days later in animal studies as shown in FIG. 23 (indicating disappearance of the gel and completion of the blood vessel). Accordingly, the gel 40 may disappear or be physically removed after about one week.

As a result of the disappearance of the gel 40, a vascular structure 37 is formed wherein the luminal surface is covered with endothelial cells 32a, and blood flows in the direction of high blood pressure to low blood pressure. That is, if the gel 40 is inserted to as to connect an ischemic portion with a healthy portion, the ample blood supply of the healthy portion flows to the anemic portion. As a result, the ischemic portion can be repaired.

(Repair of Blood Vessels of Lower Extremities)

Next, an example is indicated of using the fistula formation-inducing material according to the present invention to repair a blood vessel of a lower extremity.

Figure 24:
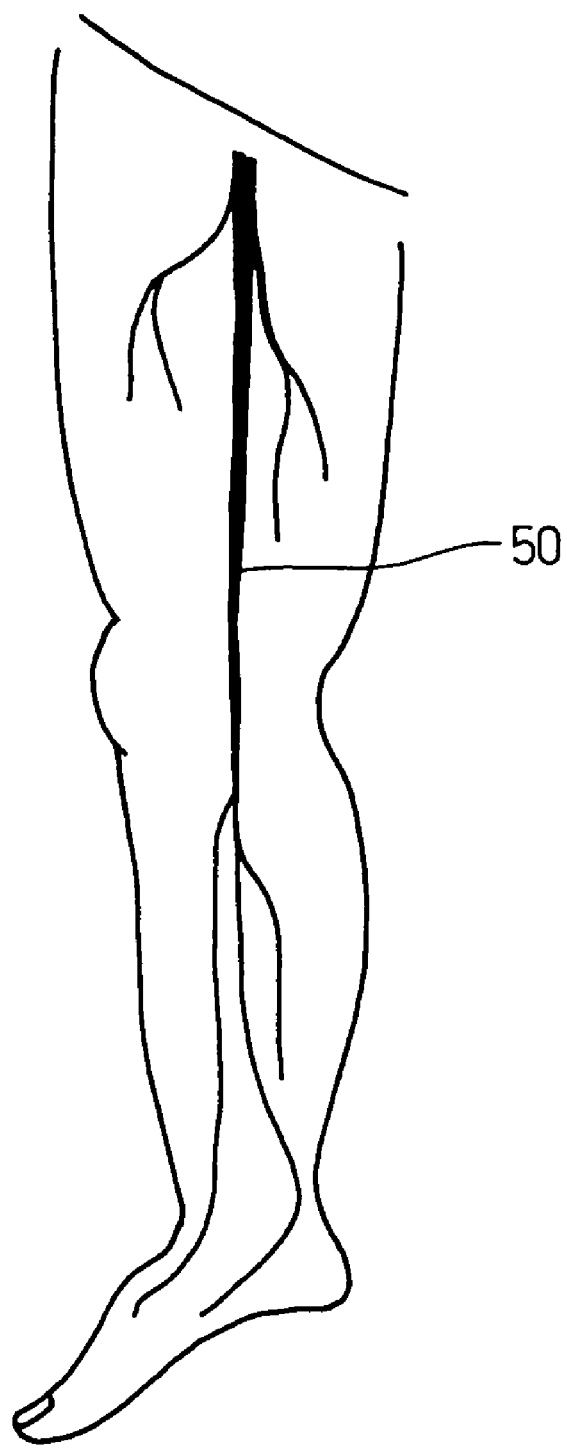
FIG. 24 is a schematic drawing showing an example of arterial branches in the normal human right leg.
Figure 25:
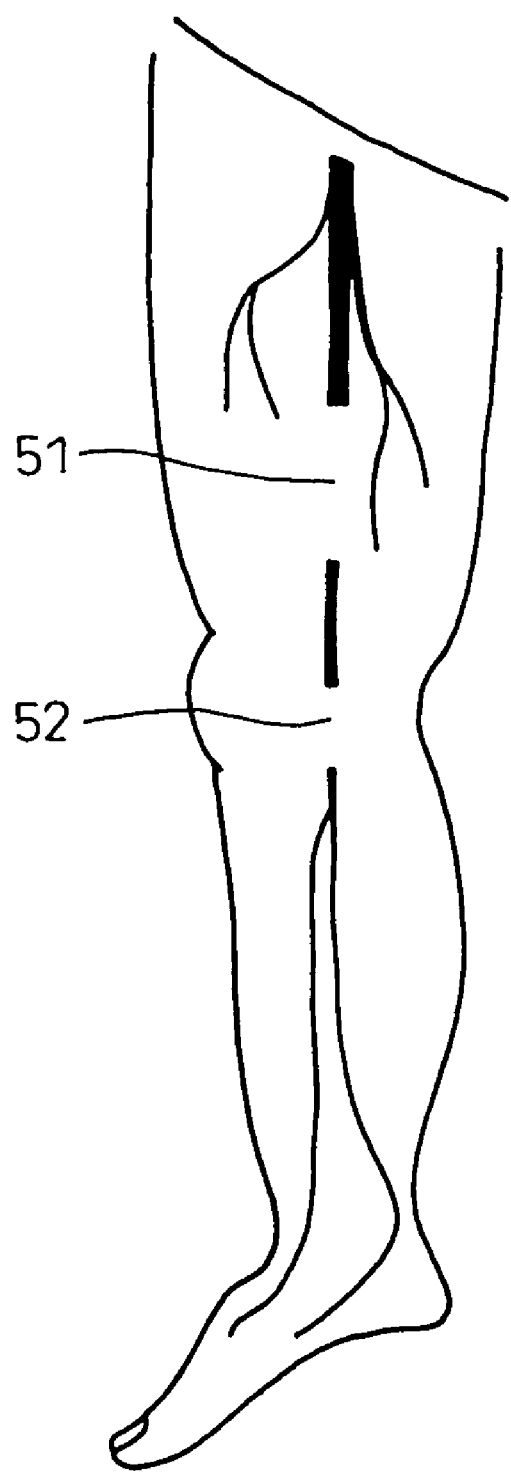
FIG. 25 is a schematic drawing showing an example of occlusion of an artery above the knee in a human right leg.

FIG. 24 shows the distribution of a main artery 50 in a normal human right leg. FIG. 25 shows a case of arteriosclerosis and diabetic vascular occlusion wherein occlusion indicated by reference symbols 51 and/or 52 in the drawing is observed. In a case of occlusion 51, bypass surgery can be performed using an artificial blood vessel, while in a case of occlusion 52, surgery can be performed using the patient's own vein.

Figure 26:
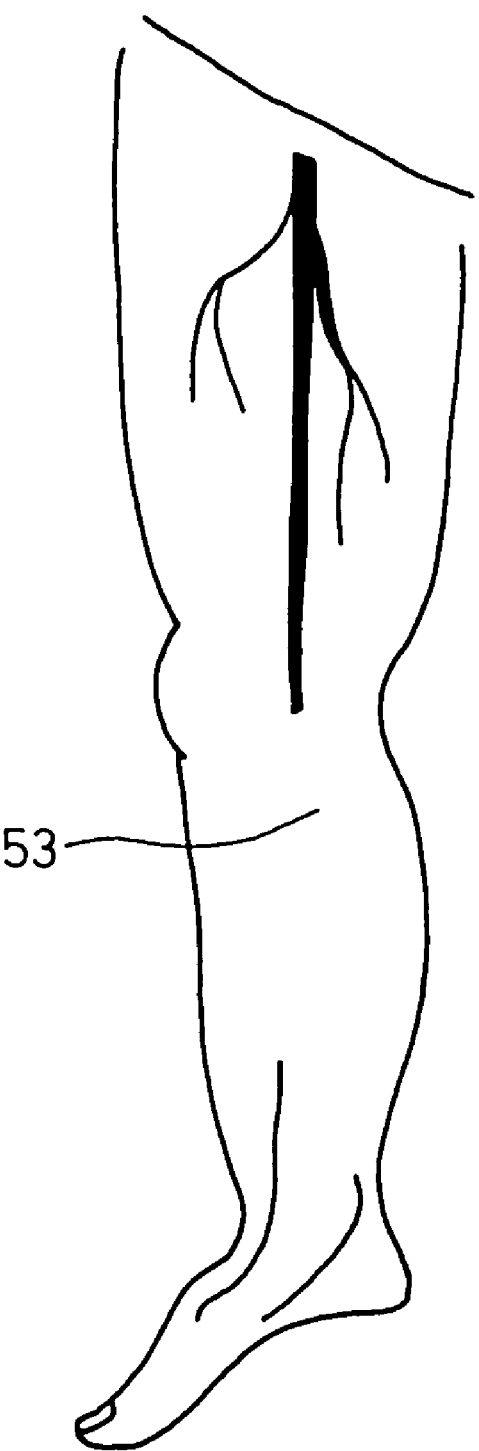
FIG. 26 is a schematic drawing showing an example of occlusion of an artery below the knee in a human right leg.
Figure 27:
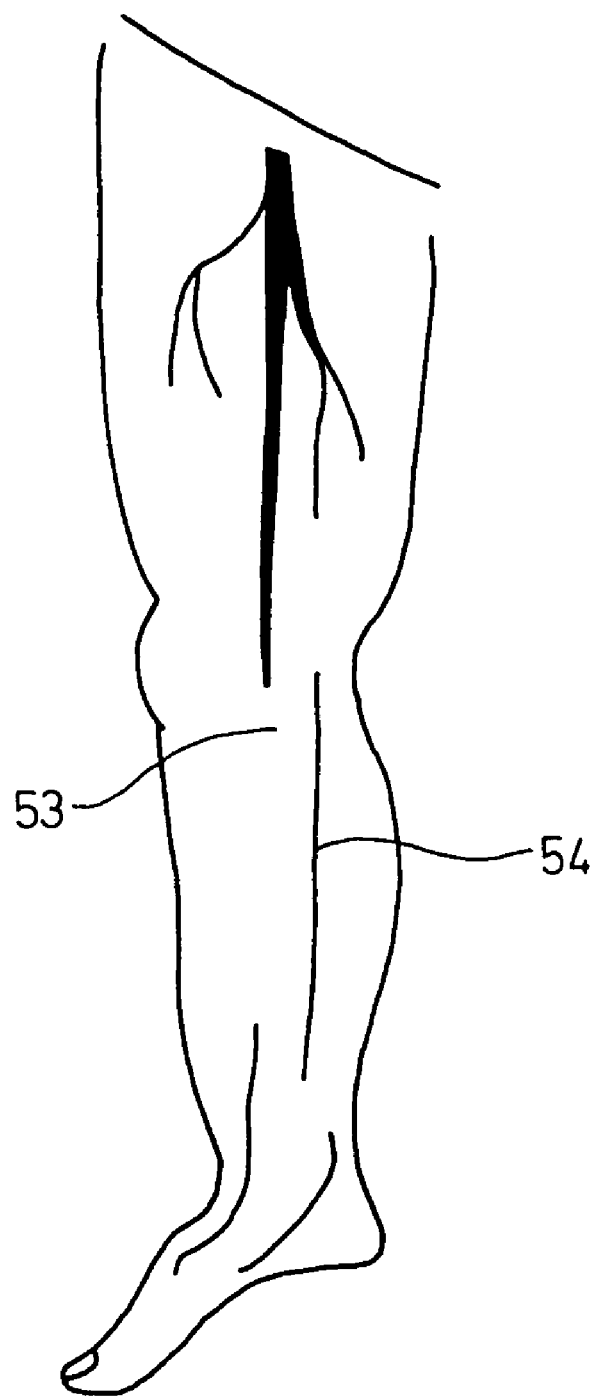
FIG. 27 is a schematic drawing showing an example of having inserted the fistula formation-inducing material in FIG. 26.

Although FIG. 26 shows a case of arterial occlusion starting below the knee, there has recently been a sudden increase in the number of patients presenting this type of occlusion. In a case where occlusion 53 as shown in FIG. 26, an artificial vessel which is used in such an application has yet to be developed, and the condition cannot be treated surgically. Accordingly, there is currently no choice but to have such patients undergo rehabilitation and wait until small, collateral circulation paths develop. However, due to the considerable distance over which occlusion is occurring, there are many cases wherein the developing collateral circulation paths do not reach the peripheral arteries below the ankle, and this frequently unfortunately results in amputation of the leg below the ankle. The technique of the present invention can be preferably applied to such patients. For example, as shown in FIG. 27, the fistula formation-inducing material according to the present invention in the form of a gel filament 54 should be inserted near the artery-deficient portion. For example, by fixing a factor (angiogenic growth factor) to this gel filament 54 so as to induce capillaries, numerous blood vessels 55 can be newly formed extending towards this gel filament 54.

Moreover, as a fistula covered with endothelial cells can also be formed around this filament 54 as one of the characteristics of the technique of the present invention, numerous capillaries are connected by means of a fistula formed in this manner, and several of these are able to connect to the remaining patent artery without being occluded. If allowed to communicate in this manner, blood can be supplied to the ankle through the fistula formed by this gel 54. That is, according to the present invention, a vascular network can be formed so as to connect to peripheral blood vessels formed by inducing collateral circulation paths.

(Principle of Vascular Network Formation)

Figure 29:
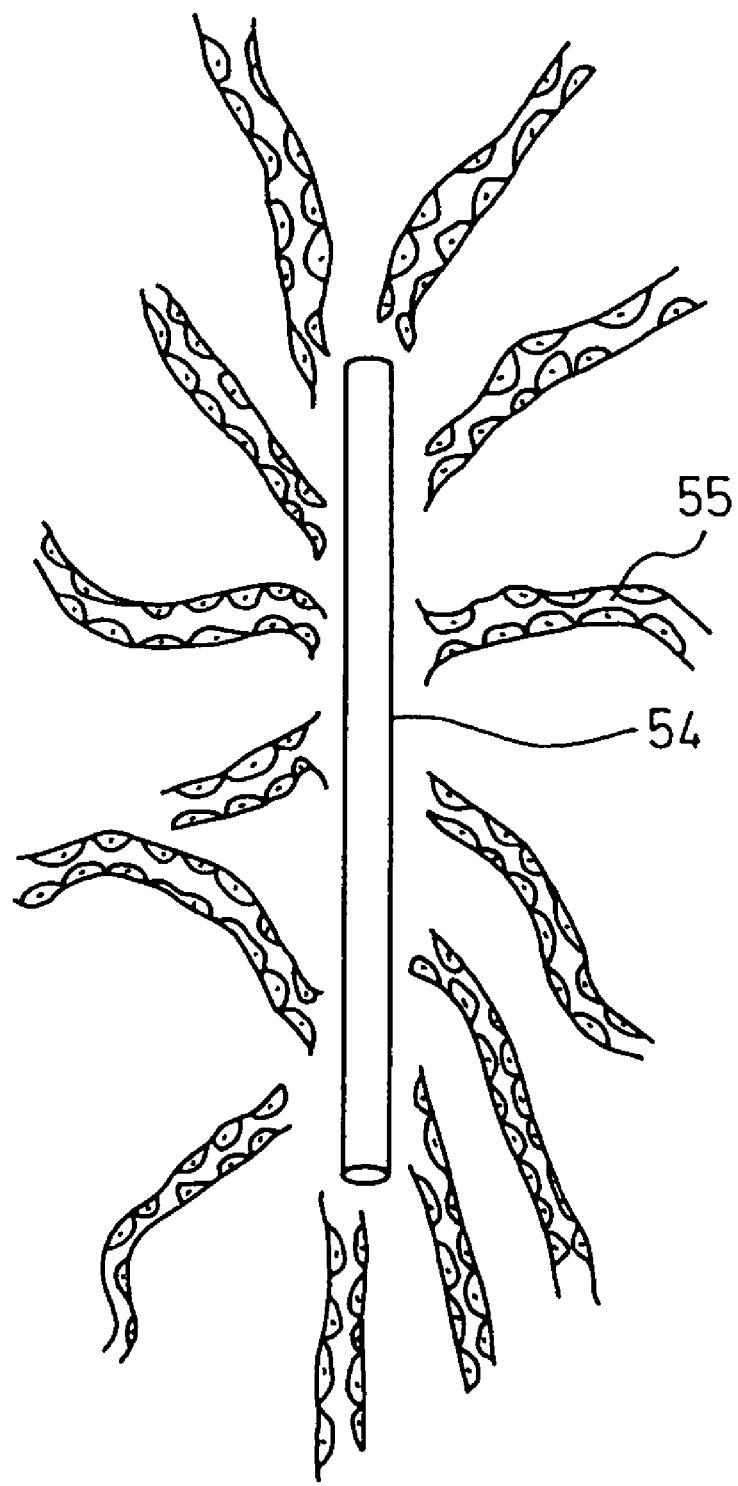
FIG. 29 is a schematic cross-sectional view showing an example of capillary ingrowth towards the fistula formation-inducing material according to the present invention.
Figure 30:
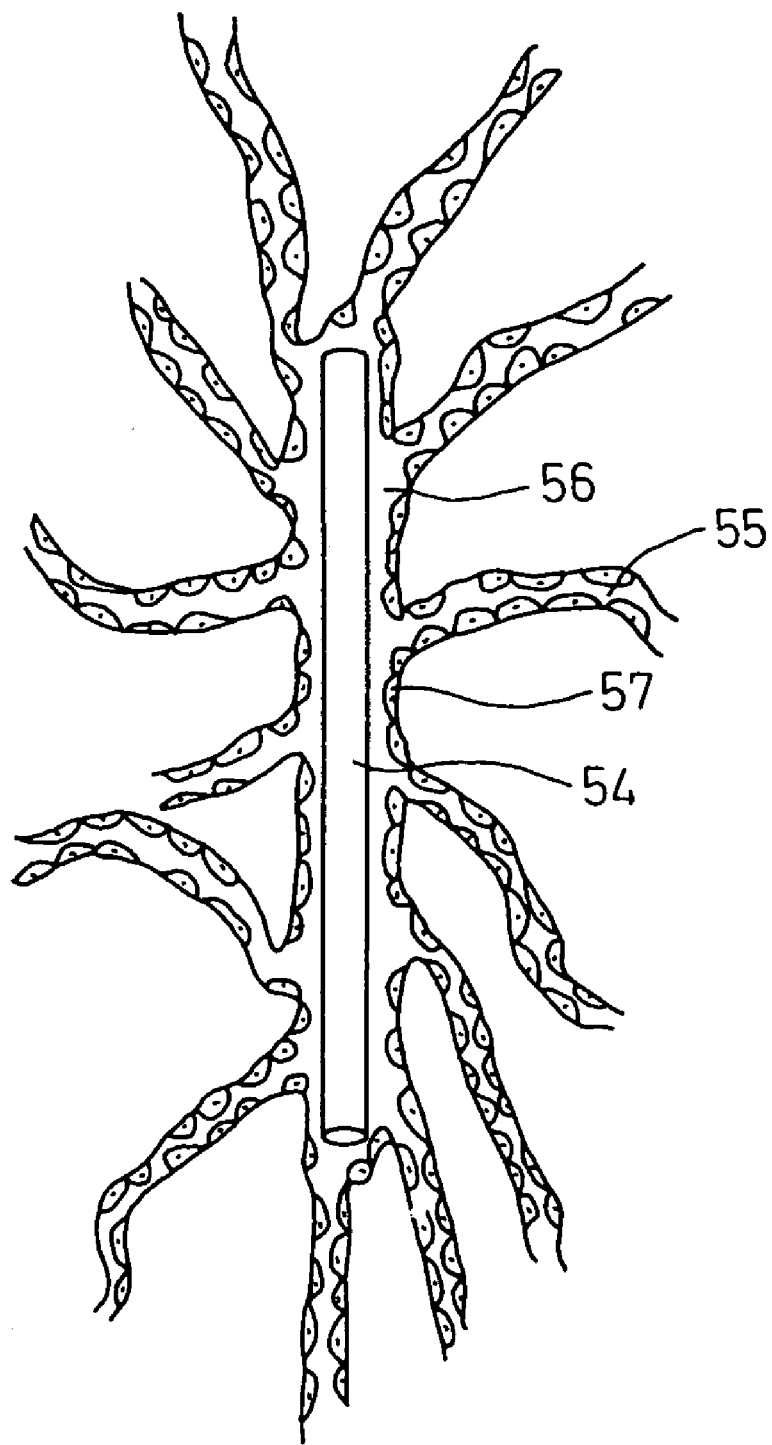
FIG. 30 is a schematic cross-sectional view showing an example of the state wherein the luminal surface of a capsular space formed by the fistula formation-inducing material according to the present invention is covered with endothelial cells. The capillary blood vessels around the fistula are connected with each other.

As shown in FIG. 29 and when, for example, a gel 54 fixed with an angiogenic growth factor is inserted into a tissue, the angiogenic growth factor is gradually released, and a large number of capillaries 55 are newly formed from the periphery extending towards the gel 54. When a large number of blood vessels gather around the gel 54 in this manner, as the gel 54 normally has cellular non-adherence, a capsule fistula 56 is formed around the gel 54. When the severed ends of the gathered capillaries 55 first reach this capsule fistula 56 and open into this capsule fistula 56, endothelial cells 57 that form the capillaries begin to cover the luminal surface of capsule fistula 56 around the gel 54. As a result, a fistula is newly formed around the gel 54 which is covered with endothelial cells 57. This fistula 56 is in the state of a so-called blood vessel and due to this phenomenon, the newly formed capillaries 55 that have gathered mutually have a "transportation network" like a "hub".

Figure 28:
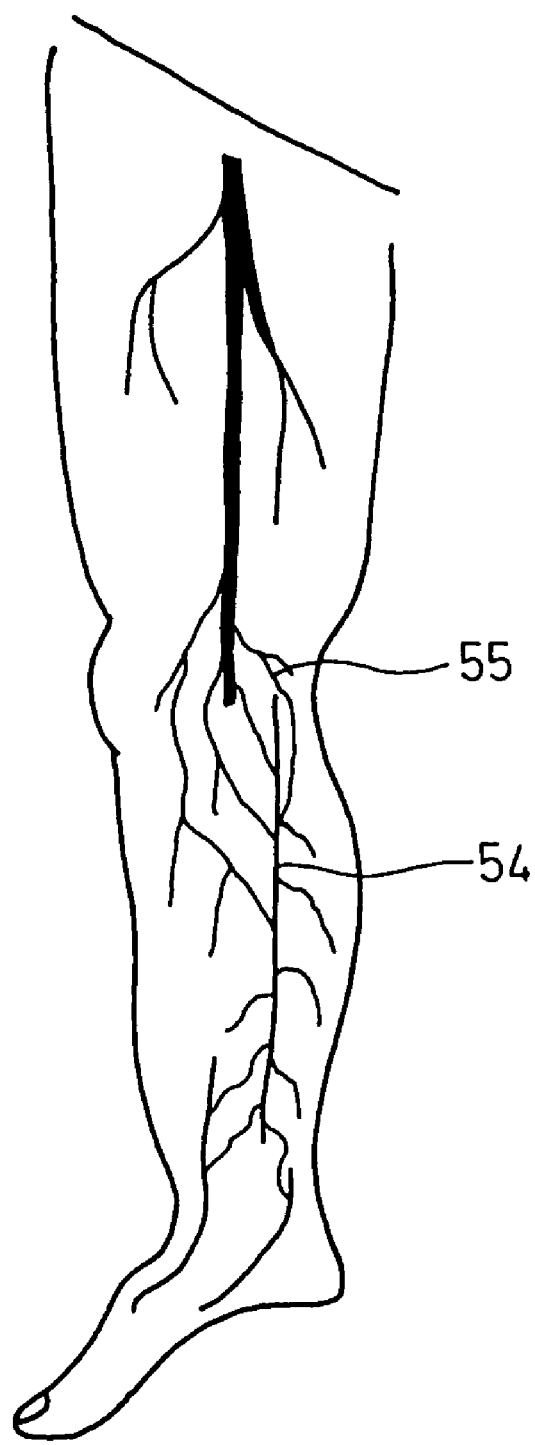
FIG. 28 is a schematic drawing showing an example of connecting numerous capillaries to a fistula formed by the fistula formation-inducing material.
Figure 31:
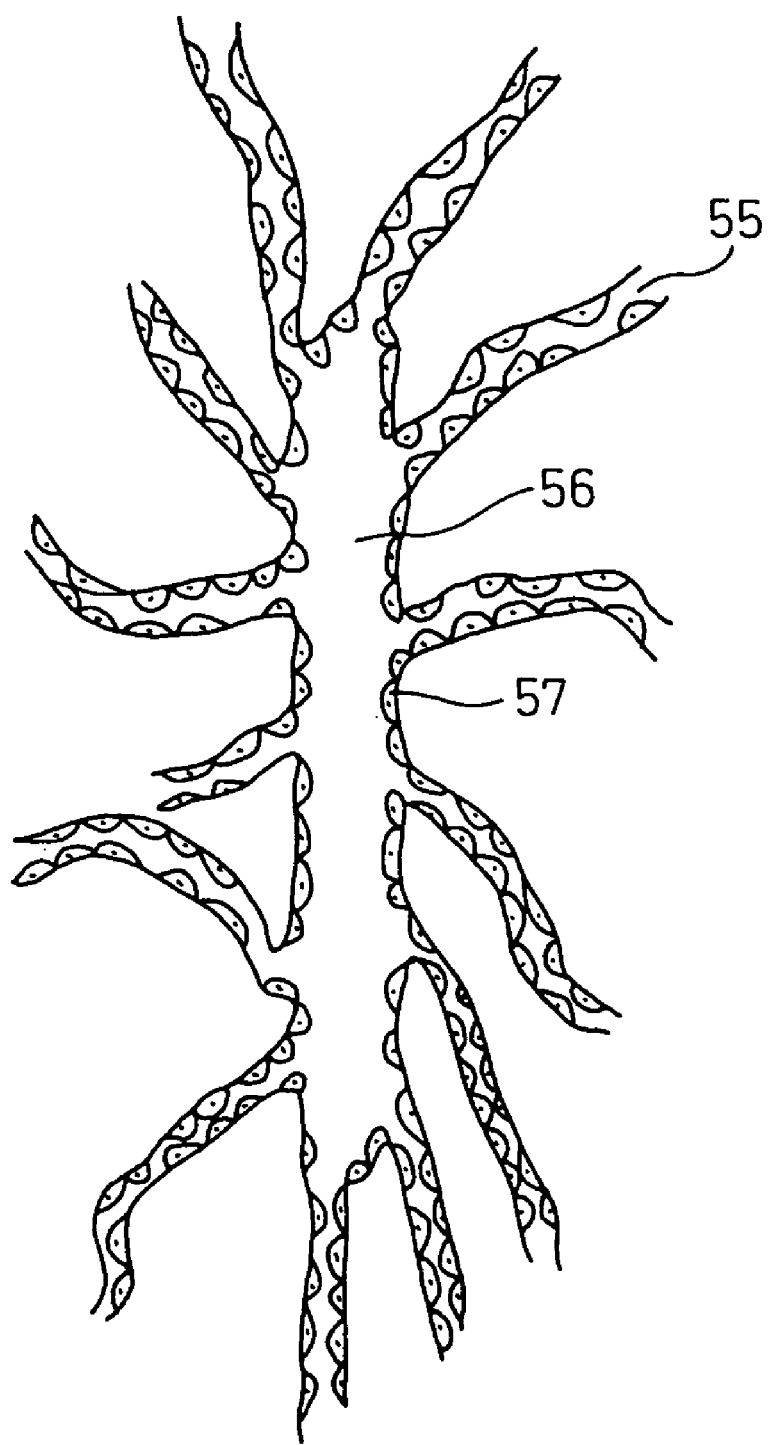
FIG. 31 is a schematic cross-sectional view showing an example of a creation of a new blood vessel wherein the fistula formation-inducing material is eliminated from FIG. 30.
Figure 32:
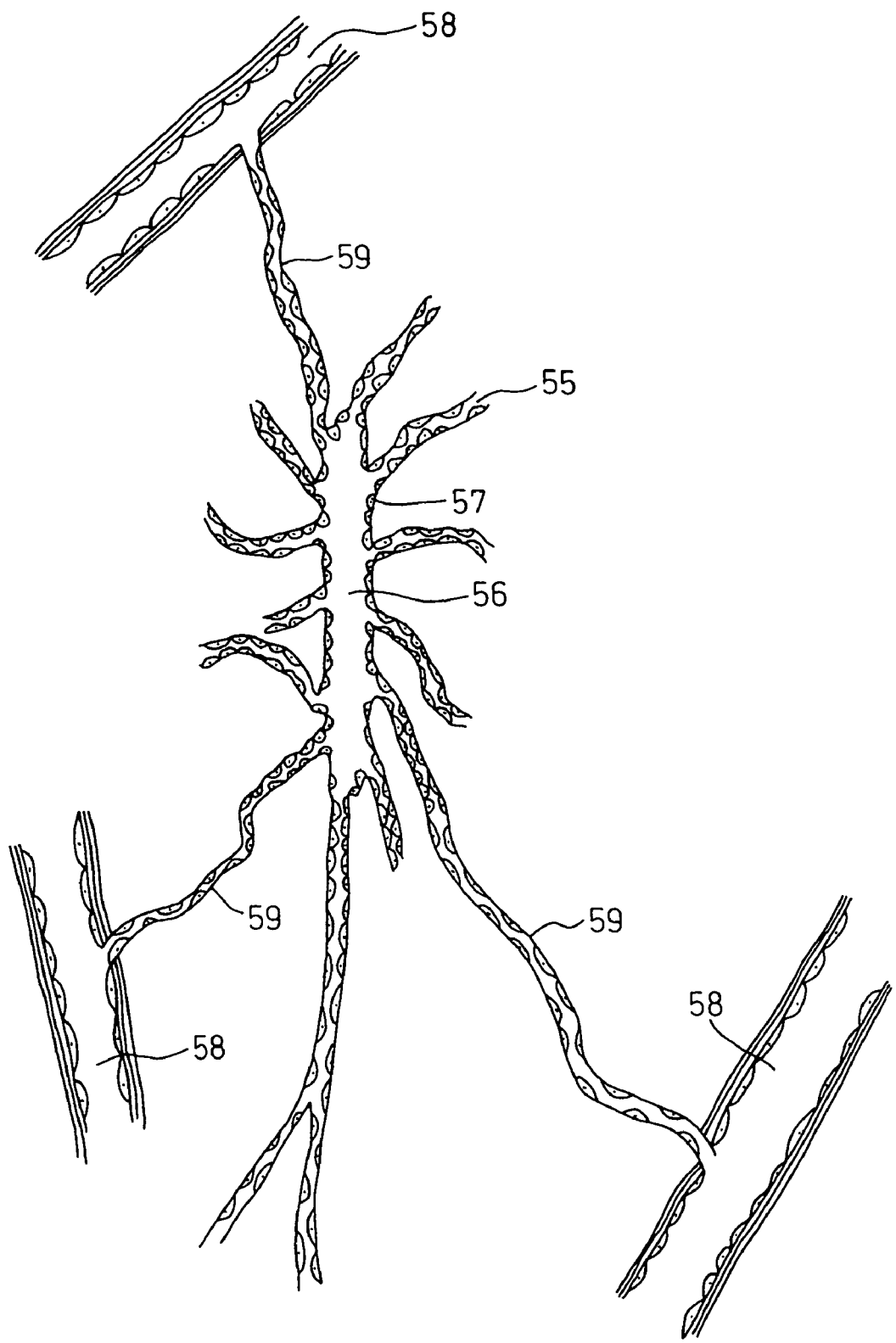
FIG. 32 is a schematic cross-sectional view showing an example of connecting an existing collateral circulation path to the fistula, i.e., a newly created blood vessel, of FIG. 31.

When this state has been reached, the gel filament 54 is allowed to disappear (by, for example, absorption). Alternatively, if the gel 54 is removed surgically, as shown in FIG. 31, fistula 56 in the form of a newly formed blood vessel is formed wherein the luminal surface is completely covered by endothelial cells 57. That is, a vascular network in the form of a "hub" is formed wherein a long blood vessel 56 and a large number of capillaries 55 extending thereto are connected. This being the case, this vascular network can also have a connection with a portion of a collateral circulation path 59 extending from a patent artery 58 which is not occluded. As a result, a satisfactory transportation network can be formed with surrounding blood vessels. This then can become the "vascular network formed so as to connect to peripheral blood vessels able to be formed by inducing collateral circulation paths" as shown in FIG. 28.

Hereinbelow, the present invention will be described in more detail with reference to specific Examples.

EXAMPLES

Example 1

A mixed solution (mixing ratio: 1:1:1) of 2% hyaluronic acid (trade name: Sodium Hyaluronate, made from cockscomb, Wako Pure Chemical Industries, Osaka), 0.02% protamine (trade name: Protamine Sulfate, made from salmon, Wako Pure Chemical Industries, Osaka) and 0.02% heparin (trade name: Sodium Heparin, made of porcine liver, Wako Pure Chemical Industries, Osaka) was prepared in deionized distilled water and then forming a gel filament from this mixed solution. More specifically, this gel filament was formed in the manner described below.

The above-mentioned gel material was placed in a 5 ml syringe and cooled, without attaching the syringe needle, to 0° C. This was then extruded in 100% ethanol to obtain a frozen gel filament.

After the resulting gel filament was freeze-dried, it was crosslinked with an epoxy compound (EX-313, Nagase Chemical, Osaka). This freeze-drying and crosslinking were specifically carried out in the manner described below.

That is, freeze-drying was carried out by drying the above-mentioned gel filament under reduced pressure for 3 hours after cooling to −20° C. using a Freeze Dryer manufactured by Tokyo Rika Kogyo (Tokyo). Crosslinking was carried out by preparing an ethanol solution of 3% epoxy compound, and placing the above-mentioned gel filament in this solution, and then heating to 50° C. for 3 hours.

The gel filament formed in the above manner had a thickness of 1 mm and length of 4 cm, and could be easily inserted into a 16 gauge elaster needle (trade name: Ther-Flow 16G× 2'/2, Telmo Corp.).

An adult dog (beagle, female, age 3 years) was laparotimized under general pentobarbital anesthesia and then exposure of the heart and insertion of the above-mentioned elaster needle into wall of the left ventricle. Moreover, the gel filament prepared above was implanted in the ventricle wall by inserting the gel filament (thickness: 1 mm) into the elaster needle. The length of the gel filament was 4 cm. Following implantation of the gel filament, the elaster needle was extracted while leaving only the gel filament in the heart by using a pusher rod corresponding to the thickness of the inner needle of the elaster needle.

Following this procedure, antibiotic (trade name: Cefamezin, Fujisawa Pharmaceutical, administered by intramuscular injection, dose: 100 mg/kg) was administered to prevent infection, and the above-mentioned dog was maintained by feeding ordinary dog food. After two weeks had elapsed, the heart of the animal was excised and observed macroscopically and microscopically (magnification: 10-400×). As a result, the gel filament had disappeared, and a tissue fistula measuring 4 cm in length and 1 mm in inner diameter had formed at the site where the gel was inserted. Blood was observed to be flowing through the fistula formed in this manner, and no thrombus tissue was observed in the fistula.

As a result of observing by light microscopy (Nikon, magnification: 200×), the wall of the fistula formed by cells growing on the surface of the above-mentioned fistula formation-inducing material was covered with vascular endothelial cells observed on the luminal surface of ordinary vascular walls. On the basis of these findings, the tissue fistula was determined to be functioning as a blood vessel. That is, a blood vessel was clearly demonstrated to have been formed as intended.

Example 2

A dog (beagle, female, age 5 years) with liver cirrhosis (liver cirrhosis induced artificially by administration of carbon tetrachloride) was obtained for the test animal. The portal pressure of this dog was elevated to about 50 mmHg (measuring device: Multipurpose Observation System with Manometer, Nihon Kohden, Tokyo).

The following documents can be referred to regarding the above-mentioned induction of liver cirrhosis: Nature (http:/// www.natureasia.com/japan/research-h/medicine/archive/ 0107) (downloaded on Dec. 3, 2001) July, 2001 "Intrinsic cannabinoids acting on vascular CBI receptors were involved in vasodilation observed in advanced liver cirrhosis", http:// www02.so-net.ne.jp/-miyashit/06.html (downloaded on Dec. 3, 2001);

Brandao C G, Ferriera H H, Piovesana H.: "Therapeutic effects of DDB on viral chronic hepatitis B". Polimeno N C, Ferraz J G, de Nucci G, Pedrazzoli J Jr.: Development of an experimental model of liver cirrhosis in rabbits. Clin Exp Pharmacol Physiol. 200 Dec.; 27(12): 987-90. Kawasaki H.: Development of tumor in the course of spontaneous restoration of carbon tetrachloride induced cirrhosis of the liver in rats. Kurume Med J. 1965; 12(1): 37-42. Stenger R J.: Concentric lamellar formations in hepatic parenchymal cells of carbon tetrachloride-treated rats. J. Ultrastruct Res. 1966 Feb; 14(3): 240-53. A gel filament measuring 4 cm in length and 2 mm thickness was formed according to the same method as in Example 1.

Although the gel filament was inserted into the cardiac wall in Example 1, in the present example, the above-mentioned gel filament (length: 4 cm, thickness: 2 mm) was inserted from the portal region towards the central portion of the left lobe of the liver within the liver of the above-mentioned liver cirrhosis-induced dog using the same method as Example 1. Following implantation of the gel filament, the elaster needle was extracted in the same manner as Example 1.

When portal pressure was measured after two months had elapsed following this procedure, portal pressure was found to have decreased to 25 mmHg. When 5 ml of contrast medium (trade name: Angio-Conray, Daiichi Pharmaceutical, Osaka) were injected and then X-ray imaging, a new vessel was observed to have formed at the portion where the gel filament was inserted, and a bypass vessel was determined to have formed between the portal system and venous system within the liver.

When the liver of the above-mentioned dog was excised and observed by light microscopy (magnification: 200×), the gel filament at that portion had already disappeared, and new blood vessels were determined to have formed within the liver.

Example 3

A mixed solution (mixing ratio: 1:1) of 2% hyaluronic acid (trade name: Sodium Hyaluronate, made from cockscomb, Wako Pure Chemical Industries, Osaka) and 4% dextran (trade name: Dextran 400,000, Wako Pure Chemical Industries, Osaka) was prepared, and a gel filament was formed using this mixed solution in the same manner as Example 1. Moreover, after this gel filament was freeze-dried in the same manner as Example 1, it was insolubilized by immersing for 10 minutes at room temperature in an alcohol (ethanol) solution of iron chloride at a concentration of 1 M to form a metal complex of hyaluronic acid in the gel.

The gel filament formed in this manner had a thickness of 1.5 mm and length of 4 cm, and could be inserted into a 14 gauge elaster needle.

A procedure was performed on the liver of a rabbit (male, age 1 year) wherein the outflow of bile at the acting portion was inhibited by selectively ligating the intra-hepatic bile duct using 1-0 polyester suture at the site corresponding to the left lobe. As a result, discharge of bile from the left portion of the liver became extremely poor and the liver became enlarged at that portion.

One week after the above-mentioned procedure, the gel filament formed as described above was inserted into the liver using a 14 gauge elaster needle so as to infiltrate into the right lobe from the left lobe. After the gel filament was implanted, the elaster needle was extracted while leaving only the gel filament in the liver by using a pusher rod corresponding to the thickness of the inner needle of the elaster needle.

When the liver was examined after 2 weeks had elapsed following the above-mentioned procedure, a fistula had formed in the liver located at the portion where the gel filament had been inserted, and the gel filament had already been degraded and absorbed. Bile was flowing through this newly formed fistula, and as a result, a new bile outflow path was formed within the liver. In this manner, the enlargement of the left side of the liver had disappeared. Examination by light microscopy (magnification: 200×) revealed that the walls of this newly formed bile outflow path were covered by the same cells as those present on the luminal surface of a normal intrahepatic bile duct.

Example 4

A mixed solution (mixing ratio: 1:1) of 2% hyaluronic acid (trade name: Sodium Hyaluronate, made from cockscomb, Wako Pure Chemical Industries, Osaka) and 2% heparin (trade name: Sodium Heparin, made from porcine liver, Wako Pure Chemical Industries, Osaka) was prepared, and a gel filament was formed using this mixed solution in the same manner as Example 1. This gel filament was then insolubilized by immersing in a 0.1 M iron chloride alcohol solution to form a metal complex of hyaluronic acid in the same manner as Example 3. The gel filament formed in this manner had a thickness of 0.5 mm and length of 2 cm, and could be inserted into a 20 gauge elaster needle.

A tendon sheath from the leg of a chicken (female, age 4 months) was opened under sterile conditions in compliance with general surgical procedures and, after removing a part of the tendon sheath, the above-mentioned gel filament was inserted along with an elaster needle to completely close the tendon sheath.

Next, after implanting the gel filament in the elaster, the elaster needle was extracted while gradually pushing in a pushing rod into the elaster, thereby implanting the gel filament in the partially removed portion of the tendon sheath.

When the tendon sheath portion was opened after two weeks had elapsed following the above-mentioned procedure, there was no adhesion of the tendon and a new tendon sheath had formed at this portion. The inserted gel had already disappeared. Observation by light microscopy (magnification: 200×) revealed that mesothelial cells that cover the luminal surface of normal tendon sheath were covering the newly formed tendon sheath portion.

Example 5

A mixed solution (mixing ratio: 1:1:1) of 2% hyaluronic acid, 0.02% protamine and 0.02% heparin was prepared in the same manner as Example 1, and a gel filament was prepared using this mixed solution in the same manner as Example 1 and then crosslinking with an epoxy compound (EX-313, Nagase Chemical, Osaka) after freeze-drying. The formed filament was compressed manually to form a fiber having a thickness of 0.4 mm, and a straight, long needle (Nipro Corp., length: 63 mm, thickness: 1.10 mm) was attached to the end of the fiber using a vascular indwelling catheter needle (trade name: Hakko Elaster Type 2, Hakko Medical).

A procedure was performed on dogs (beagles, male, age 2 years) wherein the connective tissue at the base of the left front limb was completely removed, including the lymph nodes. The thickness of the left and right front limbs were measured after one month had elapsed following the above-mentioned procedure, and the following procedure was performed on those dogs that demonstrated a significant increase in the thickness of the limb on the left side on which the procedure had been performed.

The fiber that had been formed and attached to the needle was passed through the subcutaneous tissue and muscle from the forelimb portion of the front limbs to the anterior thoracic region, and 10 fibers were sutured and then implanting 10 gel filaments at that site. This procedure was performed for a state of poor flow of lymph and other tissue fluid.

When the thickness of the forelimbs was examined after one month had elapsed following the above-mentioned procedure, each forelimb was found to have decreased in thickness by about 10%. When trypan blue stain (trade name: Trypan Blue, Wako Pure Chemical Industries, Osaka) was injected into the subcutaneous tissue, a path through which the stain flowed was determined to have been formed in the portion where the fiber was sutured. Observation by light microscopy (magnification: 80×) revealed that an extremely narrow fistula had formed in that portion, and that tissue fluid was flowing through that portion.

Example 6

Dextran, protamine sulfate and heparin (mixing ratio: 1:1:1) were mixed in the same manner as Example 1 and then the addition of a small amount of water and kneading to form a gel filament which was then air-dried for 12 hours. The thickness of the gel filament was 2 mm and the length was 8 cm. The resulting gel filament was inserted into the subcutaneous tissue of a lower limb, the back limb, of a dog (beagle, male, age 5 years) (at a location about 15 cm from the end and to a depth of about 10 mm).

When the portion where the gel filament was inserted into the subcutaneous tissue was opened after two weeks had elapsed following insertion of the gel filament, the gel filament was found to have been absorbed, a large number of capillaries had gathered towards that portion, and a fistula had formed at the portion where the gel had been present.

When the fistula formed in this manner was observed by light microscopy (magnification: 100×), although the tissue that composed the inner fistula surface was in the form of connective tissue covered with collagen fibers and fibroblasts, approximately 50% (based on the ratio of surface area covered) of the luminal surface was covered with endothelial cells.

Example 7

After performing hydrophilic treatment on the surface of a round silicon filament (outer diameter: 3 mm, length: 8 cm) manufactured by Fuji Systems Corp. by plasma treatment (plasma treatment apparatus: pinhole tester, Tokyo High-Frequency Electric Oven Corp., plasma irradiation conditions: 30 kV, 1 MHz, 30 seconds), a gel comprising a mixture (mixing ratio: 10:1) of gelatin (trade name: Succinylated Gelatin, Koken Co. Ltd) and heparin (trade name: Sodium Heparin, Wako Pure Chemical Industries) was prepared and applied to the round silicon filament and then air-drying for 12 hours. Subsequently, the gelatin was crosslinked with ultraviolet light (ultraviolet irradiation conditions: 500 microwatts·min/cm$^2$).

The periphery of the filament formed in the above manner was covered with a mesh tube formed with polyester fibers (trade name: Microknit, Golasky Co. Ltd). The tube obtained in this manner was then inserted into the muscle of the lower limb of a dog in the same manner as Example 6 (to a depth of about 10 mm) and allowed to remain there for 3 weeks.

When an incision of about 1 cm was made in the severed end of the silicon filament and the silicon round filament was removed three weeks later, a connective tissue tube using the polyester fibers as a framework was formed around the silicon round filament. When this connective tissue was observed by light microscopy (magnification: 50-200×), although a connective tissue wall containing large amounts of collagen and fibroblasts had formed surrounding the polyester fiber mesh, a large number of capillaries were observed within the connective tissue wall. Moreover, observation of the inner fistula surface of this wall by light microscopy (magnification: 100×) revealed that roughly 55% of this portion was covered with endothelial cells. That is, a wall that resembled a vascular wall had formed.

Moreover, when the newly formed capillaries were additionally examined by observation of continuous sections (size: about 20 mm×10 mm) by light microscopy (magnification: 20× and 500×), they were determined to be connected to a comparatively large artery which was already present around the tissue. That is, the newly formed capillaries had formed a vascular network with a previously existing surrounding artery.

As has been indicated in the above-mentioned example, in the present invention, the formation of fistula tissue having one surface consisting of a smooth surface was determined to be easily obtained in a living body in a short period of time, thereby clearly demonstrating the remarkable effects of the present invention.

INDUSTRIAL APPLICABILITY

The fistula formation-inducing material according to the present invention containing a material having fibrin and/or platelet non-adherence is able to effectively inhibit adherence of fibroblasts to the surface of the material even when arranged in a living body. As a result, by placing the material in a suspended state and allowing a layer of endothelial cells and mesothelial cells to form on the tissue surface surrounding the material, the infiltration of endothelial cells to this surface is facilitated, thereby making it possible to form a cell-inductive-type of tissue fistula. The fistula formation-inducing material according to the present invention is particularly advantageous for forming a narrow fistula.

In an embodiment wherein a cell growth factor is used in combination with the fistula formation-inducing material according to the present invention, as cell activity, including cell infiltration and migration, can be aggressively and selectively induced, it becomes even easier to form tissue having an intended cell composition.

The fistula formation-inducing material according to the present invention is based on the presence of a material having fibrin and/or platelet non-adherence at least in a portion thereof, and facilitates the formation of a smooth surface on the luminal surface of the fistula which is formed.

In an embodiment wherein the fistula formation-inducing material according to the present invention is formed with a substance which is degraded and absorbed in a living body, after a fistula is formed by endothelial cells and so forth in a living body, the fistula formation-inducing material can be easily made to be substantially absorbed. Accordingly, the procedure of removing the fistula formation-inducing material can be eliminated, thereby facilitating the elimination of impairments to subsequent maintenance of fistula function.

The invention claimed is:

1. A fistula formation-inducing solid-fiber made of a hydrogel material in the form of a single fiber, having a property of forming a fistula in tissue wherein cells are exposed therein on at least a portion of the fistula luminal surface and wherein said hydrogel material is a solid fiber and the outer diameter of said solid fiber is from 0.5-6 mm.

2. A fistula formation-inducing hydrogel material according to claim 1, wherein the fistula-forming hydrogel material has fibrin and/or platelet non-adherence properties.

3. A fistula formation-inducing hydrogel material according to claim 1, which comprises a different gel material in at least a portion thereof.

4. A fistula formation-inducing hydrogel material according to claim 1, which comprises a biodegradable material in at least a portion thereof.

5. A fistula formation-inducing hydrogel material according to claim 1, wherein the fistula-forming property is based on cellular non-adherence and/or antithrombogenicity.

6. A fistula formation-inducing hydrogel material according to claim 1, which is a medical material.

7. A fistula formation-inducing hydrogel material according to claim 1, wherein the fistula formation-inducing hydrogel material can retain a factor having a physiological function, or a complex or derivative thereof.

8. A fistula formation-inducing hydrogel material according to claim 7, wherein the factor having a physiological function is an antibiotic, a protein, a lipid, a polysaccharide, an enzyme, a hormone, a cytokine, heparin, a protamine, a urokinase, an anticoagulant, a cell growth factor, a cell growth inhibitor, or a complex or derivative thereof.

9. A fistula formation-inducing hydrogel material according to claim 1, wherein the fistula formation-inducing hydrogel material is polyglycolic acid, polylactic acid, polylactic acid-polyglycolic acid copolymers, biodegradable (3-hydroxylburate-4-hydroxylbutyrate) polyester polymers, polydioxane, polyethylene glycol, collagen, gelatin, albumin, fibrin, chitosan, chitin, fibroin, cellulose, mucopolysaccharides, fibronectin, laminin, alginic acid, hyaluronic acid, heparin, heparan sulfate, chondroitin sulfate, polyamino acid, starch, dextrin, dextran, agarose, pectin, mannan or a derivative thereof.

10. A device for body insertion into the body, comprising: a hollow tubular member and a solid fiber fistula formation-inducing hydrogel material in the form of a single fiber, having an outer diameter of 0.5-6 mm, at least a portion of which is inserted into the hollow tubular member;
wherein the fistula formation-inducing hydrogel material has a property of forming a fistula wherein cells are exposed on at least a portion of the fistula luminal surface.

11. A fistula-forming method, comprising: disposing a solid fiber fistula formation-inducing hydrogel material in the form of a single fiber, having an outer diameter of from 0.5-6 mm in a tissue, retaining the fistula formation-inducing hydrogel material in the tissue for a predetermined time period, and removing and/or causing to disappear at least a portion of the fistula formation-inducing hydrogel material to thereby form a fistula in the tissue;
wherein the fistula formation-inducing hydrogel material has a property of forming a fistula wherein cells are exposed on at least a portion of the fistula luminal surface.

12. A fistula formation-inducing hydrogel material in the form of a single fiber, having a property of forming a fistula wherein cells are exposed to at least a portion of the fistula luminal surface and wherein said hydrogel material is a solid fiber and the outer diameter of the solid fiber about 0.1 mm to 8 mm thick.

13. A fistula forming solid fiber hydrogel material according to claim 1, wherein the outer diameter of the solid fiber is 3mm or less.

14. A fistula forming method according to claim 11, wherein the outer diameter of the solid fiber is 3 mm or less.

15. A fistula forming solid fiber hydrogel material according to claim 1, wherein the hydrogel in the wet state has a moisture content of 5-80%.

16. A fistula formation-inducing hydrogel solid-fiber having an outer surface with a diameter of from 0 1 mm to 8 mm
wherein said hydrogel solid-fiber has a property of forming a fistula in tissue wherein cells are exposed to said outer surface of said hydrogel solid-fiber and form at least a portion of the fistula luminal surface.

17. A fistula formation-inducing hydrogel solid-fiber according to claim 16, wherein the hydrogel in the wet state has a moisture content of 5-80%.

18. A fistula formation-inducing hydrogel solid-fiber according to claim 16, wherein the hydrogel material is polyglycolic acid, polylactic acid, polylactic acid-polyglycolic acid copolymers, biodegradable (3-hydroxylburate-4-hydroxylbutyrate) polyester polymers, polydioxane, polyethylene glycol, collagen, gelatin, albumin, fibrin, chitosan, chitin, fibroin, cellulose, mucopolysaccharides, fibronectin, laminin, alginic acid, hyaluronic acid, heparin, heparan sulfate, chondroitin sulfate, polyamino acid, starch, dextrin, dextran, agarose, pectin, mannan or a derivative thereof.

* * * * *